(12) United States Patent
Sibbitt, Jr. et al.

(10) Patent No.: US 8,920,442 B2
(45) Date of Patent: Dec. 30, 2014

(54) VASCULAR OPENING EDGE EVERSION METHODS AND APPARATUSES

(75) Inventors: Wilmer L. Sibbitt, Jr., Albuquerque, NM (US); Randy R. Sibbitt, Helena, MT (US)

(73) Assignee: Abbott Vascular Inc., Santa Clara, CA (US)

( * ) Notice: Subject to any disclaimer, the term of this patent is extended or adjusted under 35 U.S.C. 154(b) by 1082 days.

(21) Appl. No.: 11/508,662

(22) Filed: Aug. 23, 2006

(65) Prior Publication Data

US 2007/0049968 A1 Mar. 1, 2007

Related U.S. Application Data

(63) Continuation-in-part of application No. 11/316,775, filed on Dec. 23, 2005, now abandoned.

(60) Provisional application No. 60/726,985, filed on Oct. 14, 2005, provisional application No. 60/711,279, filed on Aug. 24, 2005.

(51) Int. Cl.
*A61B 17/04* (2006.01)
*A61B 17/10* (2006.01)
*A61B 17/00* (2006.01)

(52) U.S. Cl.
CPC ... *A61B 17/0057* (2013.01); *A61B 2017/00349* (2013.01); *A61B 2017/00668* (2013.01); *A61B 2017/00637* (2013.01); *A61B 2017/00663* (2013.01); *A61B 2017/00862* (2013.01); *A61B 2017/00004* (2013.01); *A61B 2017/00672* (2013.01); *A61B 17/10* (2013.01)
USPC .......................................... 606/149; 606/139

(58) Field of Classification Search
USPC .......................... 606/139, 144, 145, 148, 149
See application file for complete search history.

(56) References Cited

U.S. PATENT DOCUMENTS

| | | |
|---|---|---|
| 287,046 A | 10/1883 | Norton |
| 312,408 A | 2/1885 | Wackerhagen |
| 438,400 A | 10/1890 | Brennen |
| 597,165 A | 1/1898 | Hall |
| 659,422 A | 10/1900 | Shidler |

(Continued)

FOREIGN PATENT DOCUMENTS

| | | |
|---|---|---|
| CA | 2 339 060 | 2/2000 |
| DE | 912619 | 5/1954 |

(Continued)

OTHER PUBLICATIONS

U.S. Appl. No. 60/693,531, filed Jun. 24, 2005, Carly.

(Continued)

*Primary Examiner* — Dianne Dornbusch

(74) *Attorney, Agent, or Firm* — Workman Nydegger; Randy Shen

(57) ABSTRACT

Tissue eversion apparatuses and methods suitable for use, as examples, with vascular closure devices. The tissue eversion apparatuses comprise a tissue engaging element, disposed within a delivery sheath. The delivery sheath protects the tissue engaging element and the surrounding tissue during use. The tissue engaging element can extend from the sheath and engage the tissue near an aperture in a tissue wall. Motion of the tissue engaging element away from the tissue can urge the tissue wall near the aperture to evert from the tissue wall, allowing, as examples, aperture closure apparatuses and methods to be conveniently employed.

19 Claims, 14 Drawing Sheets

(56) References Cited

U.S. PATENT DOCUMENTS

| | | | |
|---|---|---|---|
| 989,231 A | 4/1911 | Davis | |
| 1,088,393 A | 2/1914 | Backus | |
| 1,242,139 A | 10/1917 | Callahan | |
| 1,331,401 A | 2/1920 | Summers | |
| 1,574,362 A | 9/1922 | Callahan | |
| 1,480,935 A | 1/1924 | Gleason | |
| 1,596,004 A | 8/1926 | De Bengoa | |
| 1,625,602 A | 4/1927 | Gould et al. | |
| 1,647,958 A | 11/1927 | Ciarlante | |
| 1,880,569 A | 10/1932 | Weis | |
| 1,940,351 A | 3/1933 | Howard | |
| 2,012,776 A | 8/1935 | Roeder | |
| 2,087,074 A | 7/1937 | Tucker | |
| 2,131,321 A | 10/1937 | Hart | |
| 2,108,206 A * | 2/1938 | Meeker | 606/148 |
| 2,127,903 A | 8/1938 | Bowen | |
| 2,254,620 A | 9/1941 | Miller | |
| 2,316,297 A | 4/1943 | Southerland et al. | |
| 2,371,978 A | 3/1945 | Perham | |
| 2,397,823 A | 4/1946 | Walter | |
| RE22,857 E | 3/1947 | Ogburn | |
| 2,453,227 A | 11/1948 | James | |
| 2,595,086 A | 11/1948 | Larzelere | |
| 2,583,625 A | 1/1952 | Bergan | |
| 2,588,589 A | 3/1952 | Tauber | |
| 2,610,631 A | 9/1952 | Calicchio | |
| 2,646,045 A | 7/1953 | Priestley | |
| 2,684,070 A | 7/1954 | Kelsey | |
| 2,692,599 A | 10/1954 | Creelman | |
| 2,910,067 A | 10/1959 | White | |
| 2,941,489 A | 6/1960 | Fischbein | |
| 2,944,311 A | 7/1960 | Schneckenberger | |
| 2,951,482 A | 9/1960 | Sullivan | |
| 2,959,172 A | 11/1960 | Held | |
| 2,969,887 A | 1/1961 | Darmstadt et al. | |
| 3,015,403 A | 1/1962 | Fuller | |
| 3,033,156 A | 5/1962 | Verlish | |
| 3,104,666 A | 9/1963 | Hale et al. | |
| 3,113,379 A | 12/1963 | Frank | |
| 3,120,230 A | 2/1964 | Skold | |
| 3,142,878 A | 8/1964 | Santora | |
| 3,197,102 A | 7/1965 | Bates et al. | |
| 3,209,754 A | 10/1965 | Brown | |
| 3,348,595 A | 10/1967 | Stevens, Jr. | |
| 3,357,070 A | 12/1967 | Sloan | |
| 3,359,983 A | 12/1967 | Northey | |
| 3,413,397 A | 11/1968 | Bierbaum et al. | |
| 3,422,181 A | 1/1969 | Chirgwin, Jr. | |
| 3,470,875 A | 10/1969 | Johnson | |
| 3,482,428 A | 12/1969 | Kapitanov et al. | |
| 3,494,533 A | 2/1970 | Green et al. | |
| 3,523,351 A | 8/1970 | Filia | |
| 3,586,002 A | 6/1971 | Wood et al. | |
| 3,587,115 A | 6/1971 | Shiley | |
| 3,604,425 A | 9/1971 | Le Roy | |
| 3,618,447 A | 11/1971 | Goins | |
| 3,630,205 A | 12/1971 | Listner | |
| 3,653,388 A | 4/1972 | Tenckhoff | |
| 3,665,926 A | 5/1972 | Flores | |
| 3,677,243 A | 7/1972 | Nerz | |
| 3,682,180 A | 8/1972 | McFarlane | |
| 3,757,629 A | 9/1973 | Schneider | |
| 3,776,237 A | 12/1973 | Hill et al. | |
| 3,802,438 A | 4/1974 | Wolvek | |
| 3,805,337 A | 4/1974 | Branstetter | |
| 3,814,104 A * | 6/1974 | Irnich et al. | 607/128 |
| 3,820,544 A | 6/1974 | Semm | |
| 3,828,791 A | 8/1974 | Santos | |
| 3,840,017 A | 10/1974 | Violante | |
| 3,856,016 A | 12/1974 | Davis | |
| 3,856,018 A | 12/1974 | Perisse et al. | |
| 3,874,388 A | 4/1975 | King et al. | |
| 3,878,848 A | 4/1975 | Hiebert | |
| 3,908,662 A | 9/1975 | Razgulov et al. | |
| 3,918,455 A | 11/1975 | Coplan | |
| 3,926,194 A | 12/1975 | Greenberg et al. | |
| 3,939,820 A | 2/1976 | Grayzel | |
| 3,944,114 A | 3/1976 | Coppens | |
| 3,985,138 A | 10/1976 | Jarvik | |
| 4,011,872 A * | 3/1977 | Komiya | 606/47 |
| 4,014,492 A | 3/1977 | Rothfuss | |
| 4,018,228 A | 4/1977 | Goosen | |
| 4,018,229 A | 4/1977 | Komiya | |
| 4,064,881 A | 12/1977 | Meredith | |
| 4,109,658 A | 8/1978 | Hughes | |
| 4,128,100 A | 12/1978 | Wendorff | |
| 4,135,623 A | 1/1979 | Thyen | |
| 4,161,951 A | 7/1979 | Scanlan, Jr. | |
| 4,162,673 A | 7/1979 | Patel | |
| 4,168,073 A | 9/1979 | LaRue | |
| 4,169,476 A | 10/1979 | Hiltebrandt | |
| 4,182,339 A | 1/1980 | Hardy, Jr. | |
| 4,185,636 A | 1/1980 | Gabbay et al. | |
| 4,189,808 A | 2/1980 | Brown | |
| 4,192,315 A | 3/1980 | Hilzinger et al. | |
| 4,201,215 A | 5/1980 | Crossett et al. | |
| 4,204,541 A | 5/1980 | Kapitanov | |
| 4,207,870 A | 6/1980 | Eldridge | |
| 4,214,587 A | 7/1980 | Sakura, Jr. | |
| 4,215,699 A | 8/1980 | Patel | |
| 4,216,776 A | 8/1980 | Downie et al. | |
| 4,217,665 A | 8/1980 | Bex et al. | |
| 4,217,902 A | 8/1980 | March | |
| 4,235,177 A | 11/1980 | Arbuckle | |
| 4,235,238 A | 11/1980 | Ogiu et al. | |
| 4,267,995 A | 5/1981 | McMillan | |
| 4,278,091 A | 7/1981 | Borzone | |
| 4,316,469 A | 2/1982 | Kapitanov | |
| 4,317,445 A | 3/1982 | Robinson | |
| 4,318,401 A | 3/1982 | Zimmerman | |
| 4,327,485 A | 5/1982 | Rix | |
| 4,345,606 A | 8/1982 | Littleford | |
| 4,368,736 A | 1/1983 | Kaster | |
| 4,396,139 A | 8/1983 | Hall et al. | |
| 4,411,654 A | 10/1983 | Boarini et al. | |
| 4,412,832 A | 11/1983 | Kling et al. | |
| 4,428,376 A | 1/1984 | Mericle | |
| 4,437,465 A | 3/1984 | Nomoto et al. | |
| 4,440,170 A | 4/1984 | Golden et al. | |
| 4,469,101 A | 9/1984 | Coleman et al. | |
| 4,480,356 A | 11/1984 | Martin | |
| 4,485,816 A | 12/1984 | Krumme | |
| 4,492,229 A | 1/1985 | Grunwald | |
| 4,493,323 A | 1/1985 | Albright et al. | |
| 4,501,276 A * | 2/1985 | Lombardi | 600/376 |
| RE31,855 E | 3/1985 | Osborne | |
| 4,505,273 A | 3/1985 | Braun et al. | |
| 4,505,274 A | 3/1985 | Speelman | |
| 4,523,695 A | 6/1985 | Braun et al. | |
| 4,525,157 A | 6/1985 | Valaincourt | |
| 4,526,174 A | 7/1985 | Froehlich | |
| 4,553,543 A | 11/1985 | Amarasinghe | |
| 4,586,503 A | 5/1986 | Kirsch et al. | |
| 4,586,614 A | 5/1986 | Ger | |
| 4,587,969 A | 5/1986 | Gillis | |
| 4,592,498 A | 6/1986 | Braun et al. | |
| 4,596,559 A | 6/1986 | Fleishhacker | |
| 4,607,638 A | 8/1986 | Crainich | |
| 4,610,248 A | 9/1986 | Rosenberg | |
| 4,610,251 A | 9/1986 | Kumar | |
| 4,610,252 A | 9/1986 | Catalano | |
| 4,629,450 A | 12/1986 | Suzuki et al. | |
| 4,635,634 A | 1/1987 | Santos | |
| 4,651,733 A | 3/1987 | Mobin-Uddin | |
| 4,655,211 A | 4/1987 | Sakamoto et al. | |
| 4,665,906 A | 5/1987 | Jervis | |
| 4,687,469 A | 8/1987 | Osypka | |
| 4,697,312 A | 10/1987 | Freyer | |
| 4,702,250 A | 10/1987 | Orvil et al. | |
| 4,719,917 A | 1/1988 | Barrows et al. | |
| 4,723,549 A | 2/1988 | Wholey et al. | |
| 4,724,840 A | 2/1988 | McVay et al. | |
| 4,738,658 A | 4/1988 | Magro et al. | |
| 4,738,666 A | 4/1988 | Fuqua | |

(56) References Cited

U.S. PATENT DOCUMENTS

| | | |
|---|---|---|
| 4,744,364 A | 5/1988 | Kensey |
| 4,747,407 A | 5/1988 | Liu et al. |
| 4,748,982 A | 6/1988 | Horzewski et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,803,984 A | 2/1989 | Narayanan et al. |
| 4,830,002 A * | 5/1989 | Semm .................. 606/207 |
| 4,832,688 A | 5/1989 | Sagae et al. |
| 4,836,204 A | 6/1989 | Landymore et al. |
| 4,836,205 A | 6/1989 | Barrett |
| 4,848,341 A | 7/1989 | Ahmad |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,898,155 A | 2/1990 | Ovil et al. |
| 4,902,508 A | 2/1990 | Badylak et al. |
| 4,911,164 A | 3/1990 | Roth |
| 4,917,087 A | 4/1990 | Walsh et al. |
| 4,917,089 A | 4/1990 | Sideris |
| 4,926,860 A | 5/1990 | Stice et al. |
| 4,929,240 A | 5/1990 | Kirsch et al. |
| 4,929,246 A | 5/1990 | Sinofsky |
| 4,934,364 A | 6/1990 | Green |
| 4,935,027 A | 6/1990 | Yo on |
| 4,950,258 A | 8/1990 | Kawai et al. |
| 4,950,285 A | 8/1990 | Wilk |
| 4,957,498 A | 9/1990 | Caspari et al. |
| 4,957,499 A | 9/1990 | Lipatov et al. |
| 4,961,729 A | 10/1990 | Vaillancourt |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 4,997,436 A | 3/1991 | Oberlander |
| 4,997,439 A | 3/1991 | Chen |
| 5,002,562 A | 3/1991 | Oberlander |
| 5,002,563 A | 3/1991 | Pyka et al. |
| 5,007,921 A | 4/1991 | Brown |
| 5,009,643 A | 4/1991 | Reich et al. |
| 5,015,247 A | 5/1991 | Michelson |
| 5,021,059 A | 6/1991 | Kensey et al. |
| 5,026,390 A | 6/1991 | Brown |
| 5,032,127 A | 7/1991 | Frazee et al. |
| 5,037,433 A | 8/1991 | Wilk et al. |
| 5,041,129 A | 8/1991 | Hayhurst et al. |
| 5,047,039 A | 9/1991 | Avant et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,078,731 A | 1/1992 | Hayhurst |
| 5,080,664 A | 1/1992 | Jain |
| 5,092,941 A | 3/1992 | Miura |
| 5,100,418 A | 3/1992 | Yoon et al. |
| 5,100,419 A | 3/1992 | Ehlers |
| 5,100,422 A | 3/1992 | Berguer et al. |
| 5,100,432 A | 3/1992 | Matsutani |
| 5,108,420 A | 4/1992 | Marks |
| 5,108,421 A | 4/1992 | Fowler |
| 5,109,780 A | 5/1992 | Slouf et al. |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,129,882 A | 7/1992 | Weldon et al. |
| 5,129,912 A | 7/1992 | Noda et al. |
| 5,129,913 A | 7/1992 | Ruppert |
| 5,131,379 A | 7/1992 | Sewell, Jr. |
| 5,144,961 A | 9/1992 | Chen et al. |
| 5,147,373 A | 9/1992 | Ferzli |
| 5,147,381 A | 9/1992 | Heimerl et al. |
| 5,156,609 A | 10/1992 | Nakao et al. |
| 5,156,788 A | 10/1992 | Chesterfield et al. |
| 5,160,339 A | 11/1992 | Chen et al. |
| 5,163,946 A | 11/1992 | Li |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,176,648 A | 1/1993 | Holmes et al. |
| 5,176,691 A | 1/1993 | Pierce |
| 5,178,629 A | 1/1993 | Kammerer |
| 5,192,287 A | 3/1993 | Fournier et al. |
| 5,192,288 A | 3/1993 | Thompson et al. |
| 5,192,294 A | 3/1993 | Blake, III |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,201,744 A | 4/1993 | Jones |
| 5,207,703 A | 5/1993 | Jain |
| 5,209,756 A | 5/1993 | Seedhorm et al. |
| 5,211,650 A | 5/1993 | Noda |
| 5,217,024 A | 6/1993 | Dorsey et al. |
| 5,217,470 A | 6/1993 | Weston |
| 5,217,471 A | 6/1993 | Burkhart |
| 5,217,485 A | 6/1993 | Liv et al. |
| 5,219,358 A | 6/1993 | Bendel et al. |
| 5,222,974 A | 6/1993 | Kensey et al. |
| 5,226,908 A | 7/1993 | Yoon |
| 5,234,443 A | 8/1993 | Phan et al. |
| 5,234,445 A | 8/1993 | Walker et al. |
| 5,236,435 A | 8/1993 | Sewell, Jr. |
| 5,237,996 A * | 8/1993 | Waldman et al. .............. 600/374 |
| 5,242,427 A | 9/1993 | Bilweis |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,033 A | 10/1993 | Evans et al. |
| 5,250,053 A | 10/1993 | Snyder |
| 5,250,054 A | 10/1993 | Li |
| 5,250,058 A | 10/1993 | Miller et al. |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,269,792 A | 12/1993 | Kovac et al. |
| 5,275,616 A | 1/1994 | Fowler |
| 5,279,311 A | 1/1994 | Snyder |
| 5,281,236 A | 1/1994 | Bagnato et al. |
| 5,281,237 A | 1/1994 | Gimpelson |
| 5,281,422 A | 1/1994 | Badylak et al. |
| 5,282,808 A | 2/1994 | Kovac et al. |
| 5,282,827 A | 2/1994 | Kensey et al. |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,243 A | 3/1994 | Chodorow et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | Van Tassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,078 A | 4/1994 | Buelna |
| 5,300,085 A | 4/1994 | Yock |
| 5,304,184 A | 4/1994 | Hathaway et al. |
| 5,304,185 A | 4/1994 | Taylor |

(56) References Cited

U.S. PATENT DOCUMENTS

| | | | |
|---|---|---|---|
| 5,304,204 A | 4/1994 | Bregen | |
| 5,306,254 A | 4/1994 | Nash et al. | |
| 5,312,024 A | 5/1994 | Grant et al. | |
| 5,312,423 A | 5/1994 | Rosenbluth et al. | |
| 5,318,542 A | 6/1994 | Hirsch et al. | |
| 5,318,578 A | 6/1994 | Hasson | |
| 5,320,629 A | 6/1994 | Noda et al. | |
| 5,320,632 A | 6/1994 | Heidmueller | |
| 5,320,639 A | 6/1994 | Rudnick | |
| 5,330,445 A | 7/1994 | Haaga | |
| 5,330,491 A | 7/1994 | Walker et al. | |
| 5,334,216 A | 8/1994 | Vidal et al. | |
| 5,334,217 A | 8/1994 | Das | |
| 5,335,680 A | 8/1994 | Moore | |
| 5,336,229 A | 8/1994 | Noda | |
| 5,336,230 A | 8/1994 | Leichtling et al. | |
| 5,336,231 A | 8/1994 | Adair | |
| 5,340,360 A | 8/1994 | Stefanchik | |
| 5,342,369 A | 8/1994 | Harryman, II | |
| 5,350,399 A | 9/1994 | Erlebacher et al. | |
| 5,352,229 A | 10/1994 | Goble et al. | |
| 5,353,974 A | 10/1994 | Maurizio | |
| 5,354,279 A * | 10/1994 | Hofling | 604/164.12 |
| 5,354,312 A | 10/1994 | Brinkerhoff et al. | |
| 5,364,406 A | 11/1994 | Sewell, Jr. | |
| 5,364,407 A | 11/1994 | Poll | |
| 5,364,408 A | 11/1994 | Gordon | |
| 5,366,458 A | 11/1994 | Korthoff et al. | |
| 5,366,479 A | 11/1994 | McGarry et al. | |
| 5,368,595 A | 11/1994 | Lewis | |
| 5,368,601 A | 11/1994 | Sauer et al. | |
| 5,374,275 A | 12/1994 | Bradley et al. | |
| 5,374,278 A | 12/1994 | Chesterfield et al. | |
| 5,376,096 A | 12/1994 | Foster | |
| 5,383,896 A | 1/1995 | Gershony et al. | |
| 5,383,905 A | 1/1995 | Golds et al. | |
| 5,385,569 A | 1/1995 | Swor | |
| RE34,866 E | 2/1995 | Kensey et al. | |
| 5,387,221 A | 2/1995 | Bisgaard | |
| 5,387,227 A | 2/1995 | Grice | |
| 5,391,176 A | 2/1995 | de la Torre | |
| 5,391,182 A | 2/1995 | Chin | |
| 5,392,978 A | 2/1995 | Valez et al. | |
| 5,395,030 A | 3/1995 | Kuramoto et al. | |
| 5,395,332 A | 3/1995 | Ressemann et al. | |
| 5,395,349 A | 3/1995 | Quiachon et al. | |
| 5,397,310 A | 3/1995 | Chu et al. | |
| 5,397,325 A | 3/1995 | Delia Badia et al. | |
| 5,397,326 A | 3/1995 | Mangum | |
| 5,403,329 A | 4/1995 | Hinchcliffe | |
| 5,403,330 A | 4/1995 | Tuason | |
| 5,403,331 A | 4/1995 | Chesterfield et al. | |
| 5,403,338 A | 4/1995 | Milo | |
| 5,404,621 A | 4/1995 | Heinke | |
| 5,411,481 A | 5/1995 | Allen et al. | |
| 5,411,520 A | 5/1995 | Nash et al. | |
| 5,413,571 A | 5/1995 | Katsaros et al. | |
| 5,413,584 A | 5/1995 | Schulze | |
| 5,416,584 A | 5/1995 | Kay | |
| 5,417,699 A | 5/1995 | Klein et al. | |
| 5,419,765 A | 5/1995 | Weldon et al. | |
| 5,419,777 A | 5/1995 | Hofling | |
| 5,423,857 A | 6/1995 | Rosenman et al. | |
| 5,425,489 A | 6/1995 | Shichman et al. | |
| 5,425,705 A | 6/1995 | Evard et al. | |
| 5,425,740 A | 6/1995 | Hutchinson, Jr. | |
| 5,431,639 A | 7/1995 | Shaw | |
| 5,431,666 A | 7/1995 | Sauer et al. | |
| 5,431,667 A | 7/1995 | Thompson et al. | |
| 5,433,700 A | 7/1995 | Peters | |
| 5,433,721 A | 7/1995 | Hooven et al. | |
| 5,437,631 A | 8/1995 | Janzen | |
| 5,439,479 A | 8/1995 | Shichman et al. | |
| 5,443,477 A | 8/1995 | Marin et al. | |
| 5,443,481 A | 8/1995 | Lee | |
| 5,449,359 A | 9/1995 | Groiso | |
| 5,452,733 A | 9/1995 | Sterman et al. | |
| 5,454,822 A | 10/1995 | Schob et al. | |
| 5,454,834 A | 10/1995 | Boebel et al. | |
| 5,456,400 A | 10/1995 | Shichman et al. | |
| 5,458,574 A | 10/1995 | Machold et al. | |
| 5,462,560 A | 10/1995 | Stevens | |
| 5,462,561 A | 10/1995 | Voda | |
| 5,464,426 A | 11/1995 | Bonutti | |
| 5,466,241 A | 11/1995 | Leroy et al. | |
| 5,470,010 A | 11/1995 | Rothfuss et al. | |
| 5,470,338 A | 11/1995 | Whitfield et al. | |
| 5,474,557 A | 12/1995 | Mai | |
| 5,476,469 A | 12/1995 | Hathaway et al. | |
| 5,476,470 A | 12/1995 | Fitzgibbons, Jr. | |
| 5,478,309 A | 12/1995 | Sweezer et al. | |
| 5,478,352 A | 12/1995 | Fowler | |
| 5,478,353 A | 12/1995 | Yoon | |
| 5,478,354 A | 12/1995 | Tovey et al. | |
| 5,480,407 A | 1/1996 | Wan et al. | |
| 5,486,186 A | 1/1996 | Yoon | |
| 5,486,190 A | 1/1996 | Green | |
| 5,486,195 A | 1/1996 | Myers et al. | |
| 5,489,288 A | 2/1996 | Buelna | |
| 5,489,295 A | 2/1996 | Piplani et al. | |
| 5,492,119 A * | 2/1996 | Abrams | 600/375 |
| 5,496,332 A | 3/1996 | Sierra et al. | |
| 5,497,933 A | 3/1996 | DeFonzo et al. | |
| 5,507,744 A | 4/1996 | Tay et al. | |
| 5,507,755 A | 4/1996 | Gresl et al. | |
| 5,507,757 A | 4/1996 | Sauer et al. | |
| 5,507,758 A | 4/1996 | Thomason et al. | |
| 5,509,902 A | 4/1996 | Raulerson | |
| 5,520,655 A | 5/1996 | Davila et al. | |
| 5,520,665 A | 5/1996 | Fleetwood | |
| 5,520,702 A | 5/1996 | Sauer et al. | |
| 5,522,840 A | 6/1996 | Krajicek | |
| 5,527,321 A | 6/1996 | Hinchliffe | |
| 5,527,322 A | 6/1996 | Klein et al. | |
| D372,310 S | 7/1996 | Hartnett | |
| 5,531,700 A | 7/1996 | Moore et al. | |
| 5,536,251 A | 7/1996 | Evard et al. | |
| 5,536,267 A * | 7/1996 | Edwards et al. | 606/41 |
| 5,536,273 A | 7/1996 | Lehrer | |
| 5,540,701 A | 7/1996 | Sharkey et al. | |
| 5,540,704 A | 7/1996 | Gordon et al. | |
| 5,540,712 A | 7/1996 | Kleshinski et al. | |
| 5,540,716 A | 7/1996 | Hlavacek | |
| 5,544,802 A | 8/1996 | Crainich | |
| 5,545,171 A | 8/1996 | Sharkey et al. | |
| 5,545,178 A | 8/1996 | Kensey et al. | |
| 5,545,180 A | 8/1996 | Le et al. | |
| 5,547,474 A | 8/1996 | Kloeckl et al. | |
| 5,549,618 A | 8/1996 | Fleenor et al. | |
| 5,549,631 A | 8/1996 | Bonutti | |
| 5,554,162 A | 9/1996 | DeLange | |
| 5,560,532 A | 10/1996 | DeFonzo et al. | |
| 5,562,684 A | 10/1996 | Kammerer | |
| 5,562,686 A | 10/1996 | Sauer et al. | |
| 5,562,688 A | 10/1996 | Riza | |
| 5,562,728 A | 10/1996 | Lazarus et al. | |
| 5,567,435 A | 10/1996 | Hubbell et al. | |
| 5,569,269 A | 10/1996 | Hart et al. | |
| 5,569,271 A | 10/1996 | Hoel | |
| 5,571,120 A | 11/1996 | Yoon | |
| 5,573,540 A * | 11/1996 | Yoon | 606/139 |
| 5,573,784 A | 11/1996 | Badylak et al. | |
| 5,575,771 A | 11/1996 | Walinsky | |
| 5,584,842 A | 12/1996 | Fogarty et al. | |
| 5,584,879 A | 12/1996 | Reimold et al. | |
| 5,591,177 A | 1/1997 | Lehrer | |
| 5,591,179 A | 1/1997 | Edelstein | |
| 5,591,205 A | 1/1997 | Fowler | |
| 5,591,206 A | 1/1997 | Moufarrege | |
| 5,593,412 A | 1/1997 | Martinez et al. | |
| 5,593,421 A | 1/1997 | Bauer | |
| 5,601,602 A | 2/1997 | Fowler | |
| 5,603,718 A | 2/1997 | Xu | |
| 5,607,435 A | 3/1997 | Sachdeva et al. | |

(56) References Cited

U.S. PATENT DOCUMENTS

| | | | |
|---|---|---|---|
| 5,609,597 A | 3/1997 | Lehner | |
| 5,611,794 A | 3/1997 | Sauer et al. | |
| 5,613,974 A | 3/1997 | Andreas et al. | |
| 5,613,975 A * | 3/1997 | Christy | 606/144 |
| 5,618,291 A | 4/1997 | Thompson et al. | |
| 5,620,452 A | 4/1997 | Yoon | |
| 5,620,461 A | 4/1997 | Muijs et al. | |
| 5,624,446 A | 4/1997 | Harryman, II | |
| 5,626,588 A | 5/1997 | Sauer et al. | |
| 5,643,289 A | 7/1997 | Sauer et al. | |
| 5,643,295 A | 7/1997 | Yoon | |
| 5,643,318 A | 7/1997 | Tsukernik et al. | |
| 5,645,565 A | 7/1997 | Rudd et al. | |
| 5,645,566 A | 7/1997 | Brenneman et al. | |
| 5,645,567 A | 7/1997 | Crainich | |
| 5,647,372 A | 7/1997 | Tovey et al. | |
| 5,649,959 A | 7/1997 | Hannam et al. | |
| D383,539 S | 9/1997 | Croley | |
| 5,662,664 A | 9/1997 | Gordon et al. | |
| 5,669,917 A | 9/1997 | Sauer et al. | |
| 5,669,935 A | 9/1997 | Rosenman et al. | |
| 5,672,174 A * | 9/1997 | Gough et al. | 606/41 |
| 5,674,231 A | 10/1997 | Green et al. | |
| 5,676,689 A | 10/1997 | Kensey et al. | |
| 5,676,974 A | 10/1997 | Valdes et al. | |
| 5,681,334 A | 10/1997 | Evans et al. | |
| 5,683,405 A | 11/1997 | Yacoubian et al. | |
| 5,690,674 A | 11/1997 | Diaz | |
| 5,693,061 A | 12/1997 | Pierce et al. | |
| 5,695,504 A | 12/1997 | Gifford, III et al. | |
| 5,695,505 A | 12/1997 | Yoon | |
| 5,695,524 A | 12/1997 | Kelley et al. | |
| 5,700,273 A | 12/1997 | Buelna et al. | |
| 5,707,379 A | 1/1998 | Fleenor et al. | |
| 5,713,899 A | 2/1998 | Marnay et al. | |
| 5,713,910 A | 2/1998 | Gordon et al. | |
| 5,716,369 A | 2/1998 | Riza | |
| 5,716,375 A | 2/1998 | Fowler | |
| 5,720,574 A | 2/1998 | Barella | |
| 5,720,755 A | 2/1998 | Dakov | |
| 5,720,757 A | 2/1998 | Hathaway et al. | |
| 5,722,981 A | 3/1998 | Stevens | |
| 5,725,498 A | 3/1998 | Janzen et al. | |
| 5,725,552 A | 3/1998 | Kotula et al. | |
| 5,725,554 A | 3/1998 | Simon et al. | |
| 5,728,109 A | 3/1998 | Schulze et al. | |
| 5,728,110 A | 3/1998 | Vidal et al. | |
| 5,728,114 A | 3/1998 | Evans et al. | |
| 5,728,122 A | 3/1998 | Leschinsky et al. | |
| 5,728,132 A | 3/1998 | Van Tassel et al. | |
| 5,728,133 A | 3/1998 | Kontos | |
| 5,728,143 A * | 3/1998 | Gough et al. | 607/101 |
| 5,728,151 A | 3/1998 | Garrison et al. | |
| 5,732,872 A | 3/1998 | Bolduc et al. | |
| 5,735,736 A | 4/1998 | Volk | |
| 5,735,873 A | 4/1998 | MacLean | |
| 5,741,276 A | 4/1998 | Poloyko et al. | |
| 5,741,280 A | 4/1998 | Fleenor | |
| 5,746,755 A | 5/1998 | Wood et al. | |
| 5,749,890 A | 5/1998 | Shaknovich | |
| 5,749,898 A | 5/1998 | Schulze et al. | |
| 5,752,966 A | 5/1998 | Chang | |
| 5,755,726 A | 5/1998 | Pratt et al. | |
| 5,755,727 A | 5/1998 | Kontos | |
| 5,755,778 A | 5/1998 | Kleshinski | |
| 5,759,188 A | 6/1998 | Yoon | |
| 5,759,189 A | 6/1998 | Ferragamo et al. | |
| 5,766,183 A | 6/1998 | Sauer | |
| 5,766,186 A | 6/1998 | Faraz et al. | |
| 5,766,217 A | 6/1998 | Christy | |
| 5,766,246 A | 6/1998 | Mulhauser et al. | |
| 5,769,862 A | 6/1998 | Kammerer et al. | |
| 5,769,870 A | 6/1998 | Salahieh et al. | |
| 5,779,707 A | 7/1998 | Bertholet et al. | |
| 5,779,719 A | 7/1998 | Klein et al. | |
| 5,782,844 A | 7/1998 | Yoon et al. | |
| 5,782,860 A | 7/1998 | Epstein et al. | |
| 5,782,861 A | 7/1998 | Cragg et al. | |
| 5,792,151 A | 8/1998 | Heck et al. | |
| 5,792,152 A | 8/1998 | Klein et al. | |
| 5,795,958 A | 8/1998 | Rao et al. | |
| 5,797,928 A | 8/1998 | Kogasaka | |
| 5,797,929 A | 8/1998 | Andreas et al. | |
| 5,797,931 A | 8/1998 | Bito et al. | |
| 5,797,933 A | 8/1998 | Snow et al. | |
| 5,797,958 A | 8/1998 | Yoon | |
| 5,799,661 A | 9/1998 | Boyd et al. | |
| 5,810,776 A | 9/1998 | Bacich et al. | |
| 5,810,845 A | 9/1998 | Yoon | |
| 5,810,846 A | 9/1998 | Virnich et al. | |
| 5,810,849 A | 9/1998 | Kontos | |
| 5,810,850 A | 9/1998 | Hathaway et al. | |
| 5,810,851 A | 9/1998 | Yoon | |
| 5,814,052 A | 9/1998 | Nakao et al. | |
| 5,817,113 A | 10/1998 | Gifford, III et al. | |
| 5,820,631 A | 10/1998 | Nobles | |
| 5,824,010 A | 10/1998 | McDonald | |
| 5,824,111 A | 10/1998 | Schall et al. | |
| 5,827,298 A | 10/1998 | Hart et al. | |
| 5,830,125 A | 11/1998 | Scribner et al. | |
| 5,833,698 A | 11/1998 | Hinchliffe et al. | |
| 5,836,955 A | 11/1998 | Buelna et al. | |
| 5,836,956 A | 11/1998 | Buelna et al. | |
| 5,843,167 A | 12/1998 | Dwyer et al. | |
| 5,845,657 A | 12/1998 | Carberry et al. | |
| 5,846,253 A | 12/1998 | Buelna et al. | |
| 5,848,714 A | 12/1998 | Robson et al. | |
| 5,853,421 A | 12/1998 | Leschinsky et al. | |
| 5,853,422 A | 12/1998 | Huebsch et al. | |
| 5,855,312 A | 1/1999 | Toledano | |
| 5,855,576 A * | 1/1999 | LeVeen et al. | 606/41 |
| 5,855,585 A | 1/1999 | Kontos | |
| 5,858,082 A | 1/1999 | Cruz et al. | |
| 5,860,963 A | 1/1999 | Azam et al. | |
| 5,860,990 A | 1/1999 | Nobles et al. | |
| 5,860,991 A | 1/1999 | Klein et al. | |
| 5,861,005 A | 1/1999 | Kontos | |
| 5,865,791 A * | 2/1999 | Whayne et al. | 604/500 |
| 5,868,755 A | 2/1999 | Kanner et al. | |
| 5,868,763 A | 2/1999 | Spence et al. | |
| 5,871,474 A | 2/1999 | Hermann et al. | |
| 5,871,490 A | 2/1999 | Schulze et al. | |
| 5,871,501 A | 2/1999 | Leschinsky et al. | |
| 5,871,502 A | 2/1999 | Suryadevara | |
| 5,871,525 A | 2/1999 | Edwards et al. | |
| 5,873,876 A | 2/1999 | Christy | |
| 5,876,411 A | 3/1999 | Kontos | |
| 5,879,366 A | 3/1999 | Shaw et al. | |
| 5,891,088 A | 4/1999 | Thompson et al. | |
| 5,897,487 A | 4/1999 | Ouchi | |
| 5,897,564 A | 4/1999 | Schulze et al. | |
| 5,902,310 A | 5/1999 | Foerster et al. | |
| 5,902,311 A | 5/1999 | Andreas et al. | |
| 5,904,597 A | 5/1999 | Doi et al. | |
| 5,904,690 A | 5/1999 | Middleman et al. | |
| 5,904,697 A | 5/1999 | Gifford, III et al. | |
| 5,906,620 A | 5/1999 | Nakao et al. | |
| 5,906,631 A | 5/1999 | Imran | |
| 5,907,893 A | 6/1999 | Zadno-Azizi et al. | |
| 5,910,155 A | 6/1999 | Ratcliff et al. | |
| 5,919,207 A * | 7/1999 | Taheri | 606/219 |
| 5,921,994 A | 7/1999 | Andreas et al. | |
| 5,922,009 A | 7/1999 | Epstein et al. | |
| 5,928,266 A | 7/1999 | Kontos | |
| 5,935,147 A | 8/1999 | Kensey et al. | |
| 5,938,667 A | 8/1999 | Peyser et al. | |
| 5,941,890 A | 8/1999 | Voegele et al. | |
| 5,944,728 A * | 8/1999 | Bates | 606/127 |
| 5,947,999 A | 9/1999 | Groiso | |
| 5,951,518 A | 9/1999 | Licata et al. | |
| 5,951,547 A * | 9/1999 | Gough et al. | 606/41 |
| 5,951,576 A | 9/1999 | Wakabayashi | |
| 5,951,589 A | 9/1999 | Epstein et al. | |
| 5,951,590 A | 9/1999 | Goldfarb | |

(56) References Cited

U.S. PATENT DOCUMENTS

| | | | |
|---|---|---|---|
| 5,954,732 A | 9/1999 | Hart et al. | |
| 5,957,936 A | 9/1999 | Yoon et al. | |
| 5,957,937 A | 9/1999 | Yoon | |
| 5,957,938 A | 9/1999 | Zhu et al. | |
| 5,964,773 A | 10/1999 | Greenstein | |
| 5,964,782 A * | 10/1999 | Lafontaine et al. | 606/213 |
| 5,972,009 A | 10/1999 | Fortier et al. | |
| 5,972,030 A | 10/1999 | Garrison et al. | |
| 5,976,161 A | 11/1999 | Kirsch et al. | |
| 5,980,517 A * | 11/1999 | Gough | 606/41 |
| 5,980,539 A | 11/1999 | Kontos | |
| 5,984,934 A | 11/1999 | Ashby et al. | |
| 5,984,949 A | 11/1999 | Levin | |
| 5,984,950 A | 11/1999 | Cragg et al. | |
| 5,993,466 A * | 11/1999 | Yoon | 606/147 |
| 5,993,468 A | 11/1999 | Rygaard | |
| 5,993,476 A | 11/1999 | Groiso | |
| 5,997,555 A | 12/1999 | Kontos | |
| 6,001,109 A | 12/1999 | Kontos | |
| 6,001,110 A | 12/1999 | Adams | |
| 6,004,341 A | 12/1999 | Zhu et al. | |
| 6,007,563 A | 12/1999 | Nash et al. | |
| 6,009,877 A * | 1/2000 | Edwards | 128/898 |
| 6,010,517 A | 1/2000 | Baccaro | |
| 6,013,084 A | 1/2000 | Ken et al. | |
| 6,015,815 A | 1/2000 | Mollison | |
| 6,022,372 A | 2/2000 | Kontos | |
| 6,024,747 A * | 2/2000 | Kontos | 606/144 |
| 6,024,750 A | 2/2000 | Mastri | |
| 6,030,364 A | 2/2000 | Durgin et al. | |
| 6,030,413 A | 2/2000 | Lazarus | |
| 6,033,427 A | 3/2000 | Lee | |
| 6,036,699 A | 3/2000 | Andreas et al. | |
| 6,036,703 A | 3/2000 | Evans et al. | |
| 6,036,720 A | 3/2000 | Abrams et al. | |
| 6,042,601 A | 3/2000 | Smith | |
| 6,045,570 A | 4/2000 | Epstein et al. | |
| 6,048,351 A | 4/2000 | Gordon et al. | |
| 6,048,354 A | 4/2000 | Lawrence | |
| 6,048,357 A | 4/2000 | Kontos | |
| 6,048,358 A | 4/2000 | Barak | |
| 6,056,744 A * | 5/2000 | Edwards | 606/41 |
| 6,056,768 A | 5/2000 | Cates et al. | |
| 6,056,769 A | 5/2000 | Epstein et al. | |
| 6,056,770 A | 5/2000 | Epstein et al. | |
| 6,059,719 A | 5/2000 | Yamamoto et al. | |
| 6,059,800 A | 5/2000 | Hart et al. | |
| 6,059,825 A | 5/2000 | Hobbs et al. | |
| 6,063,085 A | 5/2000 | Tay et al. | |
| 6,063,114 A | 5/2000 | Nash et al. | |
| 6,068,603 A | 5/2000 | Suzuki | |
| 6,071,300 A | 6/2000 | Brenneman et al. | |
| 6,077,276 A | 6/2000 | Kontos | |
| 6,077,279 A | 6/2000 | Kontos | |
| 6,077,281 A | 6/2000 | Das | |
| 6,077,291 A | 6/2000 | Das | |
| 6,080,182 A | 6/2000 | Shaw et al. | |
| 6,080,183 A | 6/2000 | Tsugita et al. | |
| 6,083,242 A | 7/2000 | Cook | |
| 6,090,130 A | 7/2000 | Nash et al. | |
| 6,095,155 A | 8/2000 | Criscuolo | |
| 6,102,271 A | 8/2000 | Longo et al. | |
| 6,110,184 A | 8/2000 | Weadock | |
| 6,113,612 A | 9/2000 | Swanson et al. | |
| 6,117,125 A | 9/2000 | Rothbarth et al. | |
| 6,117,144 A | 9/2000 | Nobles et al. | |
| 6,117,145 A | 9/2000 | Wood et al. | |
| 6,117,148 A | 9/2000 | Ravo | |
| 6,117,157 A | 9/2000 | Tekulve | |
| 6,120,513 A | 9/2000 | Bailey et al. | |
| 6,120,524 A | 9/2000 | Taheri | |
| 6,126,675 A | 10/2000 | Shchervinsky et al. | |
| 6,132,439 A | 10/2000 | Kontos | |
| 6,132,440 A | 10/2000 | Hathaway et al. | |
| 6,136,010 A * | 10/2000 | Modesitt et al. | 606/144 |
| 6,139,556 A | 10/2000 | Kontos | |
| 6,143,004 A * | 11/2000 | Davis et al. | 606/144 |
| 6,149,660 A | 11/2000 | Laufer et al. | |
| 6,149,667 A | 11/2000 | Hovland et al. | |
| 6,152,144 A | 11/2000 | Lesh et al. | |
| 6,152,936 A | 11/2000 | Christy et al. | |
| 6,152,937 A | 11/2000 | Peterson et al. | |
| 6,161,263 A | 12/2000 | Anderson | |
| 6,165,204 A | 12/2000 | Levinson et al. | |
| 6,171,277 B1 | 1/2001 | Ponzi | |
| 6,171,329 B1 | 1/2001 | Shaw et al. | |
| 6,178,355 B1 * | 1/2001 | Williams et al. | 607/122 |
| 6,190,396 B1 | 2/2001 | Whitin et al. | |
| 6,193,708 B1 | 2/2001 | Ken et al. | |
| 6,193,734 B1 | 2/2001 | Bolduc et al. | |
| 6,197,042 B1 | 3/2001 | Ginn et al. | |
| 6,198,974 B1 | 3/2001 | Webster, Jr. | |
| 6,200,329 B1 | 3/2001 | Fung et al. | |
| 6,206,893 B1 | 3/2001 | Klein et al. | |
| 6,206,913 B1 | 3/2001 | Yencho et al. | |
| 6,206,931 B1 | 3/2001 | Cook et al. | |
| 6,210,407 B1 | 4/2001 | Webster | |
| 6,220,248 B1 | 4/2001 | Voegele et al. | |
| 6,221,084 B1 | 4/2001 | Fleenor | |
| 6,221,102 B1 | 4/2001 | Baker et al. | |
| 6,245,079 B1 | 6/2001 | Nobles et al. | |
| 6,248,124 B1 | 6/2001 | Pedros et al. | |
| 6,254,617 B1 | 7/2001 | Spence et al. | |
| 6,254,642 B1 | 7/2001 | Taylor | |
| 6,277,140 B2 | 8/2001 | Ginn et al. | |
| 6,280,460 B1 | 8/2001 | Bolduc et al. | |
| 6,287,322 B1 | 9/2001 | Zhu et al. | |
| 6,296,657 B1 | 10/2001 | Brucker | |
| 6,305,891 B1 | 10/2001 | Burlingame | |
| 6,306,081 B1 | 10/2001 | Ishikawa et al. | |
| 6,319,258 B1 | 11/2001 | McAllen, III et al. | |
| 6,322,580 B1 | 11/2001 | Kanner | |
| 6,328,727 B1 | 12/2001 | Frazier et al. | |
| 6,329,386 B1 | 12/2001 | Mollison | |
| 6,334,865 B1 | 1/2002 | Redmond et al. | |
| 6,348,059 B1 | 2/2002 | Hathaway et al. | |
| 6,348,064 B1 | 2/2002 | Kanner | |
| 6,355,050 B1 | 3/2002 | Andreas et al. | |
| 6,358,258 B1 * | 3/2002 | Arcia et al. | 606/139 |
| 6,375,671 B1 | 4/2002 | Kobayashi et al. | |
| D457,958 S | 5/2002 | Dycus | |
| 6,383,208 B1 | 5/2002 | Sancoff et al. | |
| 6,391,048 B1 | 5/2002 | Ginn et al. | |
| 6,395,015 B1 | 5/2002 | Borst et al. | |
| 6,397,110 B1 * | 5/2002 | Kuzma | 607/137 |
| 6,398,752 B1 | 6/2002 | Sweezer et al. | |
| 6,402,765 B1 | 6/2002 | Monassevitch et al. | |
| 6,409,739 B1 | 6/2002 | Nobles et al. | |
| 6,419,669 B1 | 7/2002 | Frazier et al. | |
| 6,423,054 B1 | 7/2002 | Ouchi | |
| 6,425,911 B1 | 7/2002 | Akerfeldt et al. | |
| 6,428,472 B1 | 8/2002 | Haas | |
| 6,428,548 B1 | 8/2002 | Durgin et al. | |
| 6,428,549 B1 | 8/2002 | Kontos | |
| 6,436,109 B1 | 8/2002 | Kontos | |
| 6,443,158 B1 | 9/2002 | Lafontaine et al. | |
| 6,443,963 B1 | 9/2002 | Baldwin et al. | |
| 6,447,540 B1 | 9/2002 | Fontaine et al. | |
| 6,450,391 B1 | 9/2002 | Kayan et al. | |
| 6,451,031 B1 | 9/2002 | Kontos | |
| 6,458,130 B1 | 10/2002 | Frazier et al. | |
| 6,461,364 B1 | 10/2002 | Ginn et al. | |
| 6,461,366 B1 * | 10/2002 | Seguin | 606/144 |
| 6,482,224 B1 | 11/2002 | Michler et al. | |
| 6,488,692 B1 | 12/2002 | Spence et al. | |
| 6,500,115 B2 | 12/2002 | Krattiger et al. | |
| 6,506,209 B2 * | 1/2003 | Ouchi | 606/206 |
| 6,506,210 B1 | 1/2003 | Kanner | |
| 6,508,828 B1 | 1/2003 | Akerfeldt et al. | |
| 6,511,489 B2 | 1/2003 | Field et al. | |
| 6,517,498 B1 * | 2/2003 | Burbank et al. | 600/564 |
| 6,517,553 B2 | 2/2003 | Klein et al. | |
| 6,517,569 B2 | 2/2003 | Mikus et al. | |
| 6,533,762 B2 | 3/2003 | Kanner et al. | |

(56) References Cited

U.S. PATENT DOCUMENTS

| | | | |
|---|---|---|---|
| 6,533,812 B2 | 3/2003 | Swanson et al. | |
| 6,537,288 B2 | 3/2003 | Vargas et al. | |
| 6,547,806 B1 | 4/2003 | Ding | |
| 6,551,319 B2 | 4/2003 | Lieberman | |
| 6,551,330 B1 | 4/2003 | Bain et al. | |
| 6,558,399 B1 | 5/2003 | Isbell et al. | |
| 6,562,052 B2 | 5/2003 | Nobles et al. | |
| 6,569,159 B1 * | 5/2003 | Edwards et al. | 606/41 |
| 6,569,173 B1 | 5/2003 | Blatter et al. | |
| 6,569,185 B2 | 5/2003 | Ungs | |
| 6,572,629 B2 | 6/2003 | Kalloo et al. | |
| 6,578,585 B1 | 6/2003 | Stachowski et al. | |
| 6,582,452 B2 | 6/2003 | Coleman et al. | |
| 6,582,482 B2 | 6/2003 | Gillman et al. | |
| 6,596,012 B2 | 7/2003 | Akerfeldt et al. | |
| 6,599,303 B1 | 7/2003 | Peterson et al. | |
| 6,599,311 B1 * | 7/2003 | Biggs et al. | 606/232 |
| 6,602,263 B1 | 8/2003 | Swanson et al. | |
| 6,610,072 B1 | 8/2003 | Christy et al. | |
| 6,613,059 B2 | 9/2003 | Schaller et al. | |
| 6,613,060 B2 | 9/2003 | Adams et al. | |
| 6,616,686 B2 | 9/2003 | Coleman et al. | |
| 6,623,509 B2 | 9/2003 | Ginn | |
| 6,623,510 B2 | 9/2003 | Carley et al. | |
| 6,626,918 B1 | 9/2003 | Ginn et al. | |
| 6,632,237 B2 | 10/2003 | Ben-David et al. | |
| 6,632,238 B2 | 10/2003 | Ginn et al. | |
| 6,634,537 B2 | 10/2003 | Chen | |
| 6,641,592 B1 | 11/2003 | Sauer et al. | |
| 6,645,205 B2 | 11/2003 | Ginn | |
| 6,652,538 B2 | 11/2003 | Kayan et al. | |
| 6,652,556 B1 | 11/2003 | VanTassel et al. | |
| 6,663,655 B2 | 12/2003 | Ginn et al. | |
| 6,669,714 B2 | 12/2003 | Coleman et al. | |
| 6,676,671 B2 | 1/2004 | Robertson et al. | |
| 6,676,685 B2 | 1/2004 | Pedros et al. | |
| 6,679,904 B2 | 1/2004 | Gleeson et al. | |
| 6,689,051 B2 | 2/2004 | Nakada et al. | |
| 6,689,147 B1 | 2/2004 | Koster, Jr. | |
| 6,695,867 B2 | 2/2004 | Ginn et al. | |
| 6,699,256 B1 | 3/2004 | Logan et al. | |
| 6,702,826 B2 | 3/2004 | Liddicoat et al. | |
| 6,712,836 B1 | 3/2004 | Berg et al. | |
| 6,712,837 B2 | 3/2004 | Akerfeldt et al. | |
| 6,716,228 B2 | 4/2004 | Tal | |
| 6,719,777 B2 | 4/2004 | Ginn et al. | |
| 6,726,704 B1 | 4/2004 | Loshakove et al. | |
| 6,736,822 B2 | 5/2004 | McClellan et al. | |
| 6,743,195 B2 | 6/2004 | Zucker | |
| 6,743,243 B1 | 6/2004 | Roy et al. | |
| 6,743,259 B2 | 6/2004 | Ginn | |
| 6,745,079 B2 * | 6/2004 | King | 607/117 |
| 6,746,457 B2 | 6/2004 | Dana et al. | |
| 6,749,621 B2 | 6/2004 | Pantages et al. | |
| 6,749,622 B2 | 6/2004 | McGuckin, Jr. et al. | |
| 6,755,842 B2 | 6/2004 | Kanner et al. | |
| 6,767,356 B2 | 7/2004 | Kanner et al. | |
| 6,776,785 B1 | 8/2004 | Yencho et al. | |
| 6,780,197 B2 | 8/2004 | Roe et al. | |
| 6,786,915 B2 | 9/2004 | Akerfeldt et al. | |
| 6,790,218 B2 | 9/2004 | Jayaraman | |
| 6,790,220 B2 | 9/2004 | Morris et al. | |
| 6,837,906 B2 | 1/2005 | Ginn | |
| 6,846,319 B2 | 1/2005 | Ginn et al. | |
| 6,849,078 B2 | 2/2005 | Durgin et al. | |
| 6,860,895 B1 | 3/2005 | Akerfeldt et al. | |
| 6,890,343 B2 | 5/2005 | Ginn et al. | |
| 6,896,687 B2 | 5/2005 | Dakov | |
| 6,896,692 B2 | 5/2005 | Ginn et al. | |
| 6,904,647 B2 | 6/2005 | Byers, Jr. | |
| 6,911,034 B2 | 6/2005 | Nobles et al. | |
| 6,926,723 B1 | 8/2005 | Mulhauser et al. | |
| 6,926,731 B2 | 8/2005 | Coleman et al. | |
| 6,939,357 B2 | 9/2005 | Navarro et al. | |
| 6,942,674 B2 | 9/2005 | Belef et al. | |
| 6,942,691 B1 | 9/2005 | Chuter | |
| 6,964,668 B2 | 11/2005 | Modesitt et al. | |
| 6,969,397 B2 | 11/2005 | Ginn | |
| 6,984,238 B2 | 1/2006 | Gifford, III et al. | |
| 6,989,003 B2 | 1/2006 | Wing et al. | |
| 6,989,016 B2 | 1/2006 | Tallarida et al. | |
| 7,001,398 B2 | 2/2006 | Carley et al. | |
| 7,001,400 B1 | 2/2006 | Modesitt et al. | |
| 7,008,435 B2 | 3/2006 | Cummins | |
| 7,008,439 B1 | 3/2006 | Janzen et al. | |
| 7,029,480 B2 | 4/2006 | Klein et al. | |
| 7,029,481 B1 | 4/2006 | Burdulis, Jr. et al. | |
| 7,033,379 B2 | 4/2006 | Peterson | |
| 7,048,747 B2 * | 5/2006 | Arcia et al. | 606/139 |
| 7,060,084 B1 | 6/2006 | Loshakove et al. | |
| 7,063,661 B2 | 6/2006 | Okada | |
| 7,063,710 B2 | 6/2006 | Takamoto et al. | |
| 7,063,711 B1 * | 6/2006 | Loshakove et al. | 606/153 |
| 7,083,635 B2 | 8/2006 | Ginn | |
| 7,108,709 B2 | 9/2006 | Cummins | |
| 7,111,768 B2 | 9/2006 | Cummins et al. | |
| 7,112,225 B2 | 9/2006 | Ginn | |
| 7,122,002 B2 | 10/2006 | Okada | |
| 7,144,411 B2 | 12/2006 | Ginn et al. | |
| 7,147,646 B2 | 12/2006 | Dana et al. | |
| 7,160,309 B2 | 1/2007 | Voss | |
| 7,163,551 B2 | 1/2007 | Anthony et al. | |
| 7,169,158 B2 | 1/2007 | Sniffin et al. | |
| 7,169,164 B2 | 1/2007 | Borillo et al. | |
| 7,179,266 B2 | 2/2007 | Kontos | |
| 7,211,101 B2 | 5/2007 | Carley et al. | |
| 7,229,458 B2 | 6/2007 | Boecker et al. | |
| 7,235,087 B2 | 6/2007 | Modesitt et al. | |
| 7,270,672 B1 | 9/2007 | Singer | |
| 7,311,720 B2 | 12/2007 | Mueller et al. | |
| 7,316,704 B2 | 1/2008 | Bagaoisan et al. | |
| 7,326,230 B2 | 2/2008 | Ravikumar | |
| 7,331,979 B2 | 2/2008 | Khosravi et al. | |
| 7,335,220 B2 | 2/2008 | Khosravi et al. | |
| 7,338,514 B2 | 3/2008 | Wahr et al. | |
| D566,272 S | 4/2008 | Walberg et al. | |
| 7,361,183 B2 | 4/2008 | Ginn | |
| 7,361,185 B2 | 4/2008 | O'Malley et al. | |
| 7,377,927 B2 | 5/2008 | Burdulis, Jr. et al. | |
| 7,390,328 B2 | 6/2008 | Modesitt | |
| 7,393,363 B2 | 7/2008 | Ginn | |
| 7,396,359 B1 | 7/2008 | Derowe et al. | |
| 7,431,727 B2 | 10/2008 | Cole et al. | |
| 7,445,626 B2 | 11/2008 | Songer et al. | |
| 7,449,024 B2 | 11/2008 | Stafford | |
| 7,462,188 B2 | 12/2008 | McIntosh | |
| 7,507,200 B2 | 3/2009 | Okada | |
| 7,533,790 B1 | 5/2009 | Knodel et al. | |
| 7,597,706 B2 | 10/2009 | Kanner et al. | |
| 7,645,285 B2 | 1/2010 | Cosgrove et al. | |
| 7,648,493 B2 | 1/2010 | Forsberg et al. | |
| D611,144 S | 3/2010 | Reynolds | |
| 7,727,249 B2 | 6/2010 | Rahmani | |
| 7,731,655 B2 * | 6/2010 | Smith et al. | 600/217 |
| 7,749,249 B2 * | 7/2010 | Gelbart et al. | 606/216 |
| 7,799,042 B2 | 9/2010 | Williamson, IV et al. | |
| 7,901,428 B2 | 3/2011 | Ginn et al. | |
| 8,226,666 B2 | 7/2012 | Zarbatany et al. | |
| 8,313,497 B2 | 11/2012 | Walberg et al. | |
| 8,469,969 B2 * | 6/2013 | Kear et al. | 606/127 |
| 8,480,687 B2 | 7/2013 | Ducharme et al. | |
| 2001/0007077 A1 | 7/2001 | Ginn et al. | |
| 2001/0031972 A1 | 10/2001 | Robertson et al. | |
| 2001/0046518 A1 | 11/2001 | Sawhney | |
| 2001/0047180 A1 | 11/2001 | Grudem et al. | |
| 2001/0053909 A1 | 12/2001 | Nakada | |
| 2002/0026215 A1 | 2/2002 | Redmond et al. | |
| 2002/0038127 A1 | 3/2002 | Blatter et al. | |
| 2002/0042622 A1 | 4/2002 | Vargas et al. | |
| 2002/0045908 A1 | 4/2002 | Nobles et al. | |
| 2002/0049427 A1 | 4/2002 | Wiener et al. | |
| 2002/0058960 A1 | 5/2002 | Hudson et al. | |
| 2002/0072768 A1 | 6/2002 | Ginn | |
| 2002/0077657 A1 | 6/2002 | Ginn et al. | |

(56) References Cited

U.S. PATENT DOCUMENTS

| | | |
|---|---|---|
| 2002/0082641 A1 | 6/2002 | Ginn et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0177876 A1 | 11/2002 | Roby et al. |
| 2002/0183786 A1 | 12/2002 | Girton |
| 2002/0188275 A1* | 12/2002 | McGuckin, Jr. ............... 604/506 |
| 2003/0004543 A1 | 1/2003 | Gleeson et al. |
| 2003/0009180 A1 | 1/2003 | Hinchliffe et al. |
| 2003/0032981 A1 | 2/2003 | Kanner et al. |
| 2003/0045893 A1 | 3/2003 | Ginn |
| 2003/0055455 A1 | 3/2003 | Yang et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093093 A1 | 5/2003 | Modesitt et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0158577 A1 | 8/2003 | Pantages et al. |
| 2003/0158578 A1 | 8/2003 | Pantages et al. |
| 2003/0187457 A1 | 10/2003 | Weber |
| 2003/0195504 A1 | 10/2003 | Tallarida et al. |
| 2003/0195529 A1 | 10/2003 | Takamoto et al. |
| 2003/0195561 A1 | 10/2003 | Carley et al. |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092964 A1 | 5/2004 | Modesitt et al. |
| 2004/0092968 A1 | 5/2004 | Caro et al. |
| 2004/0093027 A1 | 5/2004 | Fabisiak et al. |
| 2004/0097978 A1 | 5/2004 | Modesitt et al. |
| 2004/0098044 A1 | 5/2004 | Van de Moer et al. |
| 2004/0116943 A1 | 6/2004 | Brandt et al. |
| 2004/0122349 A1 | 6/2004 | Lafontaine et al. |
| 2004/0122449 A1 | 6/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0215232 A1 | 10/2004 | Belhe et al. |
| 2004/0225194 A1 | 11/2004 | Smith et al. |
| 2004/0225301 A1 | 11/2004 | Roop et al. |
| 2004/0236354 A1 | 11/2004 | Seguin |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0010248 A1 | 1/2005 | Lafontaine |
| 2005/0033359 A1 | 2/2005 | Dycus |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0143761 A1 | 6/2005 | Modesitt |
| 2005/0149117 A1 | 7/2005 | Khosravi et al. |
| 2005/0165357 A1 | 7/2005 | McGuckin et al. |
| 2005/0177189 A1 | 8/2005 | Ginn et al. |
| 2005/0187564 A1 | 8/2005 | Jayaraman |
| 2005/0216057 A1 | 9/2005 | Coleman et al. |
| 2005/0222614 A1 | 10/2005 | Ginn et al. |
| 2005/0234396 A1 | 10/2005 | Forsberg et al. |
| 2005/0234508 A1 | 10/2005 | Cummins et al. |
| 2005/0245876 A1 | 11/2005 | Khosravi et al. |
| 2005/0256532 A1 | 11/2005 | Nayak et al. |
| 2005/0261708 A1 | 11/2005 | Pasricha et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0079914 A1 | 4/2006 | Modesitt et al. |
| 2006/0089635 A1* | 4/2006 | Young et al. ............... 606/41 |
| 2006/0095029 A1* | 5/2006 | Young et al. ............... 606/41 |
| 2006/0100664 A1 | 5/2006 | Pai et al. |
| 2006/0106420 A1 | 5/2006 | Dolan et al. |
| 2006/0135989 A1 | 6/2006 | Carley et al. |
| 2006/0142785 A1 | 6/2006 | Modesitt et al. |
| 2006/0144479 A1 | 7/2006 | Carley et al. |
| 2006/0167477 A1 | 7/2006 | Arcia et al. |
| 2006/0167484 A1 | 7/2006 | Carley et al. |
| 2006/0173469 A1 | 8/2006 | Klein |
| 2006/0190014 A1 | 8/2006 | Ginn et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0287674 A1 | 12/2006 | Ginn et al. |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0032798 A1 | 2/2007 | Pantages et al. |
| 2007/0032799 A1 | 2/2007 | Pantages et al. |
| 2007/0032801 A1 | 2/2007 | Pantages et al. |
| 2007/0049967 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0083230 A1 | 4/2007 | Javois |
| 2007/0083231 A1 | 4/2007 | Lee |
| 2007/0112304 A1 | 5/2007 | Voss |
| 2007/0123817 A1 | 5/2007 | Khosravi et al. |
| 2007/0123936 A1 | 5/2007 | Goldin et al. |
| 2007/0167959 A1 | 7/2007 | Modesitt et al. |
| 2007/0179527 A1 | 8/2007 | Eskuri et al. |
| 2007/0198058 A1 | 8/2007 | Gelbart et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0276410 A1 | 11/2007 | McIntosh |
| 2007/0276416 A1 | 11/2007 | Ginn et al. |
| 2007/0276488 A1 | 11/2007 | Wachter et al. |

(56) References Cited

U.S. PATENT DOCUMENTS

| | | |
|---|---|---|
| 2007/0282352 A1 | 12/2007 | Carley et al. |
| 2007/0282354 A1 | 12/2007 | McIntosh |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0045979 A1* | 2/2008 | Ma .................. 606/144 |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0114395 A1 | 5/2008 | Mathisen et al. |
| 2008/0210737 A1 | 9/2008 | Ginn et al. |
| 2008/0221616 A1 | 9/2008 | Ginn et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287967 A1* | 11/2008 | Andreas et al. ............ 606/144 |
| 2008/0287988 A1 | 11/2008 | Smith et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319458 A1 | 12/2008 | Reynolds |
| 2008/0319475 A1 | 12/2008 | Clark |
| 2009/0005793 A1 | 1/2009 | Pantages et al. |
| 2009/0036906 A1 | 2/2009 | Stafford |
| 2009/0048615 A1 | 2/2009 | McIntosh |
| 2009/0088779 A1 | 4/2009 | Zung et al. |
| 2009/0088794 A1 | 4/2009 | LaFontaine |
| 2009/0105728 A1 | 4/2009 | Noda et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0157105 A1 | 6/2009 | Zung et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0234884 A1 | 9/2010 | Lafontaine et al. |
| 2011/0066163 A1 | 3/2011 | Cho et al. |
| 2012/0245603 A1 | 9/2012 | Voss |
| 2012/0296374 A1 | 11/2012 | Ziobro et al. |

FOREIGN PATENT DOCUMENTS

| | | |
|---|---|---|
| DE | 4210724 | 7/1993 |
| DE | 9217932 | 7/1993 |
| DE | 4220283 | 12/1993 |
| DE | 197 11 288 | 10/1998 |
| DE | 29723736 U1 | 4/1999 |
| DE | 19859952 | 2/2000 |
| DE | 10211360 | 10/2003 |
| DE | 102006056283 | 6/2008 |
| EP | 0 140 557 | 5/1985 |
| EP | 0 207 545 | 1/1987 |
| EP | 0 386 361 | 9/1990 |
| EP | 0 474 887 | 3/1992 |
| EP | 0 478 358 | 4/1992 |
| EP | 0 478 887 | 4/1992 |
| EP | 0 543 499 | 10/1992 |
| EP | 0 534 696 | 3/1993 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 756 851 | 2/1997 |
| EP | 0 774 237 | 5/1997 |
| EP | 0 812 571 | 12/1997 |
| EP | 0 858 776 | 8/1998 |
| EP | 0 941 697 | 9/1999 |
| EP | 0 941 698 | 9/1999 |
| EP | 1 867 287 | 12/2007 |
| FR | 1059544 | 3/1954 |
| FR | 2 443 238 | 7/1980 |
| FR | 2 715 290 | 7/1995 |
| FR | 2 722 975 | 2/1996 |
| FR | 2 768 324 | 3/1999 |
| FR | 2768324 | 3/1999 |
| GB | 1 358 466 | 7/1974 |
| GB | 2 075 144 | 11/1981 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 51143386 | 11/1976 |
| JP | 5220794 | 2/1977 |
| JP | 58-181006 | 12/1983 |
| JP | 12 74750 | 11/1989 |
| JP | 2119866 | 5/1990 |
| JP | 542161 | 2/1993 |
| JP | 11500642 | 8/1997 |
| JP | 2000014634 | 1/2000 |
| JP | 2000102546 | 4/2000 |
| JP | 2005218868 A | 8/2005 |
| NL | 9302140 | 7/1995 |
| PL | 171425 | 4/1997 |
| RU | 2086192 | 8/1997 |
| SU | 495067 | 12/1975 |
| SU | 820810 | 4/1981 |
| SU | 912155 | 3/1982 |
| SU | 993922 | 2/1983 |
| SU | 1093329 | 5/1984 |
| SU | 1174036 | 8/1985 |
| SU | 1243708 | 7/1986 |
| SU | 1324650 | 7/1987 |
| SU | 1405828 | 6/1988 |
| SU | 1456109 | 2/1989 |
| SU | 1544383 | 2/1990 |
| SU | 1560133 | 4/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 96/24291 | 8/1996 |
| WO | WO 96/40356 | 12/1996 |
| WO | WO 97/00046 | 1/1997 |
| WO | WO 97/03613 | 2/1997 |
| WO | WO 97/07741 | 3/1997 |

(56) References Cited

FOREIGN PATENT DOCUMENTS

| | | |
|---|---|---|
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/42262 | 10/1998 |
| WO | WO 98/58591 | 12/1998 |
| WO | WO 99/21491 | 5/1999 |
| WO | WO 99/40849 | 8/1999 |
| WO | WO 99/47049 | 9/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/12013 | 3/2000 |
| WO | WO 00/27311 | 5/2000 |
| WO | WO 00/27313 | 5/2000 |
| WO | WO 00/51498 | 9/2000 |
| WO | WO 00/56223 | 9/2000 |
| WO | WO 00/56226 * 9/2000 ............. A61B 17/04 | |
| WO | WO 00/56227 | 9/2000 |
| WO | WO 00/56228 | 9/2000 |
| WO | WO 00/69342 | 11/2000 |
| WO | WO 00/71032 | 11/2000 |
| WO | WO 01/19259 | 3/2001 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/36021 | 5/2002 |
| WO | WO 02/38055 | 5/2002 |
| WO | WO 02/45593 | 6/2002 |
| WO | WO 02/45594 | 6/2002 |
| WO | WO 02062234 | 8/2002 |
| WO | WO 02/98302 | 12/2002 |
| WO | WO 03/003925 | 1/2003 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03094748 | 11/2003 |
| WO | WO 03/099134 | 12/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/006990 | 1/2005 |
| WO | WO 2005000126 | 1/2005 |
| WO | WO 2005/023119 | 3/2005 |
| WO | WO 2005/025430 | 3/2005 |
| WO | WO 2005/030060 | 4/2005 |
| WO | WO 2005041782 | 5/2005 |
| WO | WO 2005/065549 | 7/2005 |
| WO | WO 2005063129 | 7/2005 |
| WO | WO 2005/082256 | 9/2005 |
| WO | WO 2005/092204 | 10/2005 |
| WO | WO 2005/110240 | 11/2005 |
| WO | WO 2005/115251 | 12/2005 |
| WO | WO 2005/115521 | 12/2005 |
| WO | WO 2005112782 | 12/2005 |
| WO | WO 2006/000514 | 1/2006 |
| WO | WO 2006026116 | 3/2006 |
| WO | WO 2006/052611 | 5/2006 |
| WO | WO 2006/052612 | 5/2006 |
| WO | WO 2006078578 | 7/2006 |
| WO | WO 2006/083889 | 8/2006 |
| WO | WO 2006115901 | 11/2006 |
| WO | WO 2006115904 | 11/2006 |
| WO | WO 2006118877 | 11/2006 |
| WO | WO 2007/005585 | 1/2007 |
| WO | WO 2007/019016 | 2/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 60/696,069, filed Jul. 1, 2005, Pantages et al.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
US 5,820,544, 06/1974, Semm (withdrawn).
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996,

(56) References Cited

OTHER PUBLICATIONS pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
Cardiac Catheterization and Angiography, 3rd Ed., Lea N ad Febiger, Philadelphia, 1986. Elgiloy Brochure, Jun. 23, 1959, Elgin National Watch Co., Elgin, IL.
Cardio-Thoracic Systems Prospectus dated Mar. 20, 1996.
Datascope Corporation, Montvale, NJ (1991) 1 PG, American Heart Assoc. Meeting, Anaheim.
Elgiloy Brochure, Jun. 23, 1959, Elgin National Watch Co., Elgin, IL.
Kensey Nash Corporation, Exton, PA, "The Hemostatic Puncture Closure Device", 2 pages.
Laurus Medical Corporation, "Endoscopic Suturing Made Simple," The Laurus ND-2600 Needle Driver, Irvine, CA., 1 page.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.

(56) References Cited

OTHER PUBLICATIONS

Rema-Medizintechnik GmbH, Product Brochure entitled "REMA," 7 pages.
Serruys, PW et al., A Comparision of Balloon-Expandable-Stent Implantaion With Balloon Angioplasty in Patients With Coronary Artery Disease, New England Journal of Medicine, 331:489-495, 1994.
U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/617,090, Mar. 22, 2005, Office Action.

(56) References Cited

OTHER PUBLICATIONS

U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,656, Aug. 30, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/852,190, Jun. 24, 2010, Office Action.
U.S. Appl. No. 11/958,281, Sep. 2, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, Mar. 9, 2010, Office Action.

(56) References Cited

OTHER PUBLICATIONS

U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 07/989,611, May 12, 1993, Office Action.
U.S. Appl. No. 07/989,611, Aug. 1, 1994, Office Action.
U.S. Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.
U.S. Appl. No. 08/638,076, Jan. 21, 1997, Office Action.
U.S. Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999, Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/262,402, Mar. 29, 2000, Office Action.
U.S. Appl. No. 09/262,402, May 30, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/395,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.
U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.
U.S. Appl. No. 09/988,541, Dec. 13, 2005, Notice of Allowance.
U.S. Appl. No. 10/033,689, Sep. 30, 2003, Office Action.
U.S. Appl. No. 10/152,272, Jan. 24, 2005, Office Action.
U.S. Appl. No. 10/152,272, May 13, 2005, Notice of Allowance.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.
U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/357,984, Jan. 9, 2006, Office Action.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007, Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/660,288, Apr. 29, 2009, Office Action.
U.S. Appl. No. 10/660,288, Aug. 3, 2009, Office Action.
U.S. Appl. No. 10/660,288, Mar. 30, 2010, Office Action.
U.S. Appl. No. 10/729,541, Dec. 12, 2006, Office Action.
U.S. Appl. No. 10/729,541, Jun. 18, 2007, Office Action.
U.S. Appl. No. 10/729,541, Jan. 8, 2008, Office Action.
U.S. Appl. No. 10/729,541, Sep. 23, 2008, Office Action.
U.S. Appl. No. 10/729,541, May 1, 2009, Office Action.
U.S. Appl. No. 10/729,541, Nov. 16, 2009, Notice of Allowance.
U.S. Appl. No. 10/729,541, Mar. 25, 2010, Notice of Allowance.
U.S. Appl. No. 10/729,541, Jul. 12, 2010, Notice of Allowance.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.
U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/877,974, Jul. 9, 2008, Office Action.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,531, Feb. 9, 2009, Office Action.
U.S. Appl. No. 10/909,531, Sep. 16, 2009, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 10/948,445, Jul. 11, 2007, Office Action.
U.S. Appl. No. 11/199,338, Jan. 25, 2007, Office Action.
U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2010, Notice of Allowance.
U.S. Appl. No. 11/199,515, Aug. 2, 2010, Notice of Allowance.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/273,107, Oct. 28, 2009, Office Action.
U.S. Appl. No. 11/273,107, Jun. 2, 2010, Office Action.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.

(56) References Cited

OTHER PUBLICATIONS

U.S. Appl. No. 11/363,005, Dec. 23, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/363,005, Jul. 23, 2010, Notice of Allowance.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/552,593, Mar. 22, 2010, Notice of Allowance.
U.S. Appl. No. 11/688,722, Mar. 10, 2010, Office Action.
U.S. Appl. No. 11/688,722, Jul. 29, 2010, Notice of Allowance.
U.S. Appl. No. 11/891,358, Apr. 26, 2010, Office Action.
U.S. Appl. No. 11/891,513, Apr. 9, 2010, Office Action.
U.S. Appl. No. 12/257,127, Aug. 30, 2010, Office Action.
U.S. Appl. No. 90/006,469, Nov. 29, 2002, Request for Re-Examination.
U.S. Appl. No. 90/006,469, Sep. 10, 2004, Office Action.
U.S. Appl. No. 90/006,469, Sep. 27, 2005, Notice of Re-Issue.
U.S. Appl. No. 90/006,469, Jun. 27, 2006, Re-Examination Certification.
U.S. Appl. No. 10/616,832, Sep. 20, 2010, Notice of Allowance.
U.S. Appl. No. 10/787,073, Sep. 15, 2010, Notice of Allowance.
U.S. Appl. No. 11/767,818, Sep. 30, 2010, Office Action.
U.S. Appl. No. 12/365,397, Sep. 13, 2010, Office Action.
U.S. Appl. No. 11/981,513, Sep. 28, 2010, Office Action.
U.S. Appl. No. 12/365,397, Jun. 21, 2011, Notice of Allowance.
U.S. Appl. No. 12/559,377, Aug. 3, 2012, Office Action.
U.S. Appl. No. 12/365,397, Oct. 12, 2011, Issue Notification.
U.S. Appl. No. 12/559,377, Dec. 14, 2011, Restriction Requirement.
U.S. Appl. No. 12/559,377, Feb. 27, 2012, Office Action.
U.S. Appl. No. 11/508,715, Oct. 18, 2010, OA.
U.S. Appl. No. 12/365,397, Dec. 17, 2010, OA.
U.S. Appl. No. 11/508,656, Feb. 10, 2014, Notice of Allowance.
U.S. Appl. No. 13/052,634, Feb. 8, 2013, Office Action.
U.S. Appl. No. 13/052,634, Apr. 22, 2013, Office Action.
U.S. Appl. No. 13/052,634, Nov. 8, 2013, Office Action.
U.S. Appl. No. 13/111,403, filed Jun. 28, 2013, Office Action.
U.S. Appl. No. 13/111,403, Sep. 5, 2013, Office Action.
U.S. Appl. No. 13/111,403, Dec. 24, 2013, Office Action.
U.S. Appl. No. 11/508,656, Jun. 4, 2014, Issue Notification.
U.S. Appl. No. 11/508,715, Mar. 27, 2014, Office Action.
International Search Report for PCT/US06/33033 dated Sep. 28, 2007.
International Search Report for PCT/US06/33031 dated May 19, 2008.
International Search Report for PCT/US06/33032 dated Sep. 27, 2007.

* cited by examiner

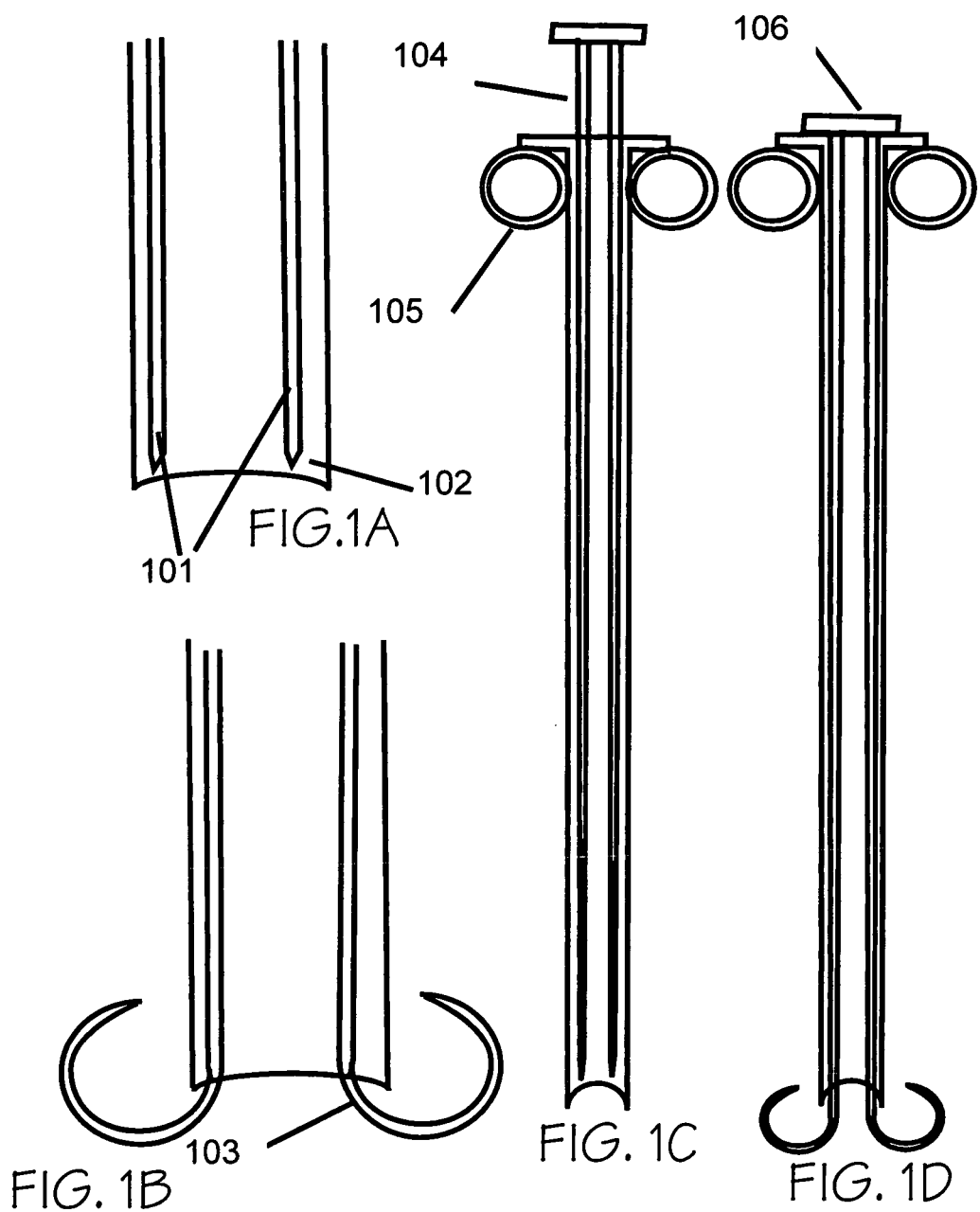

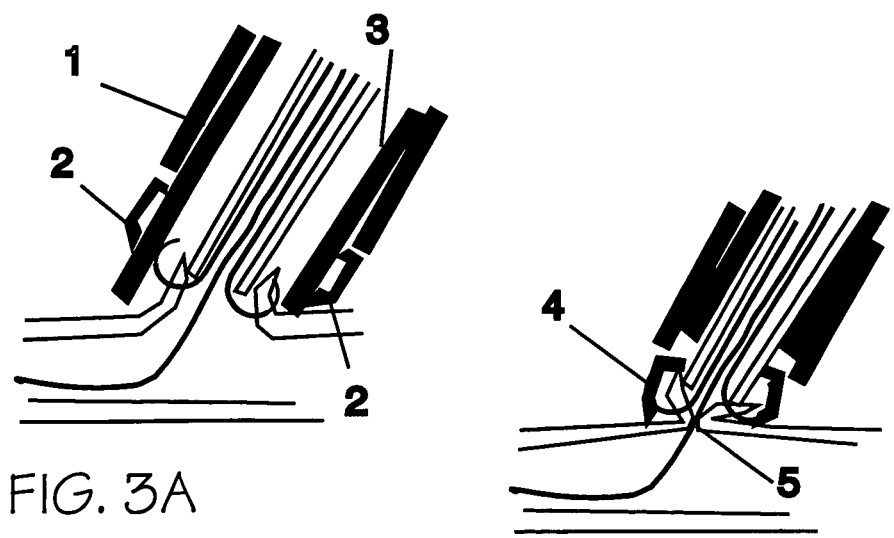
FIG. 3A
FIG. 3B
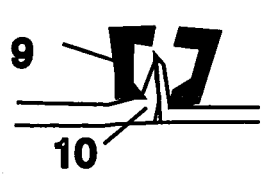
FIG. 3D
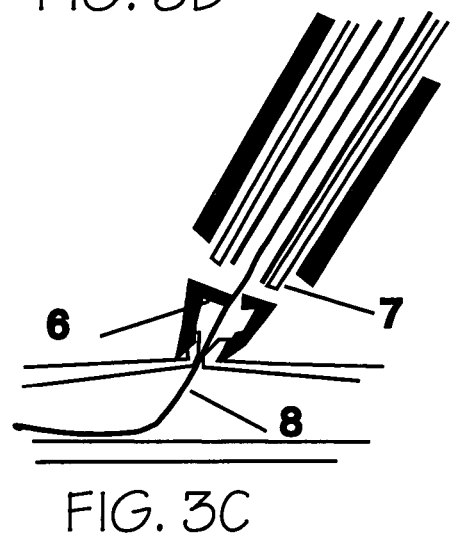
FIG. 3C

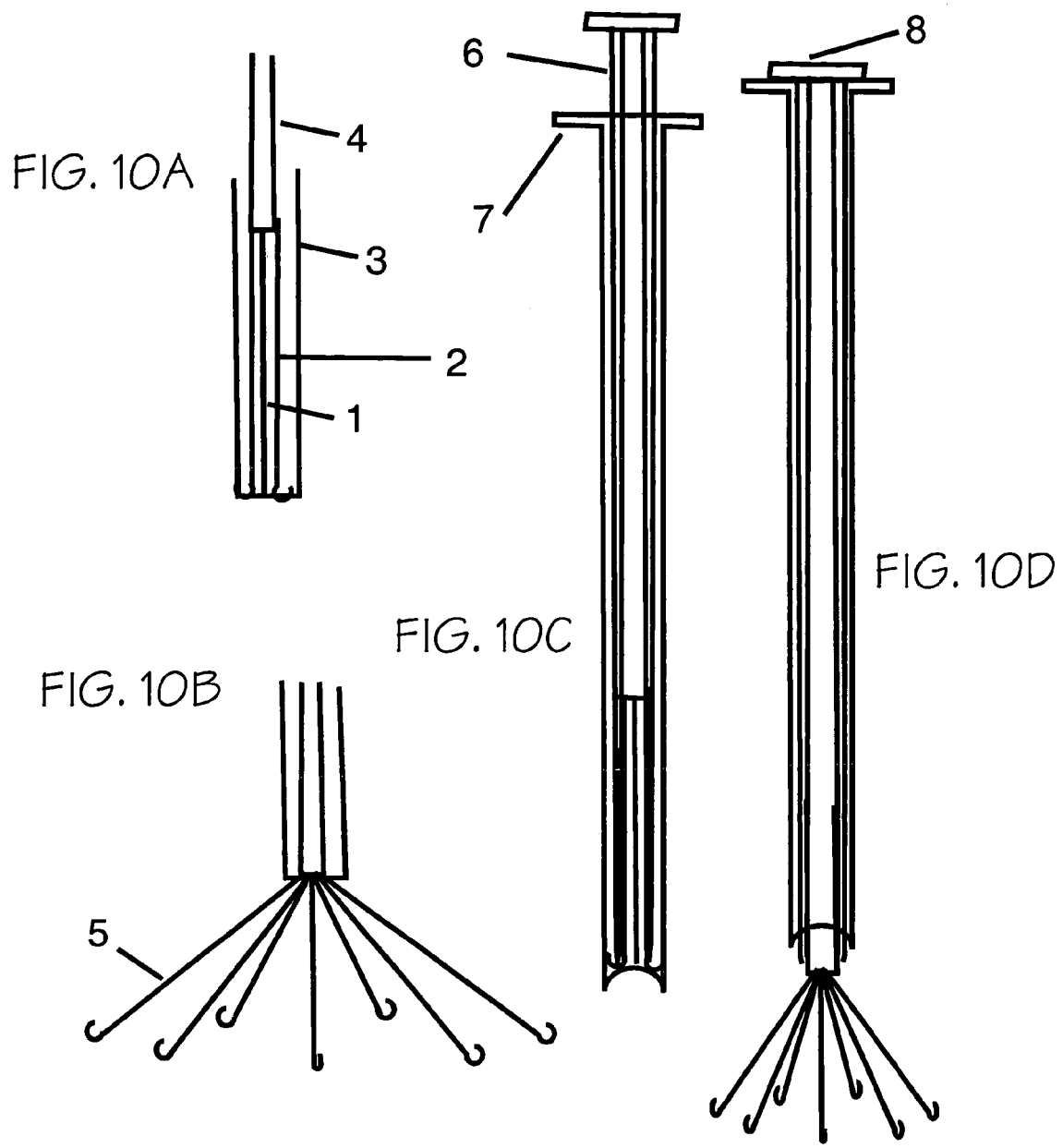

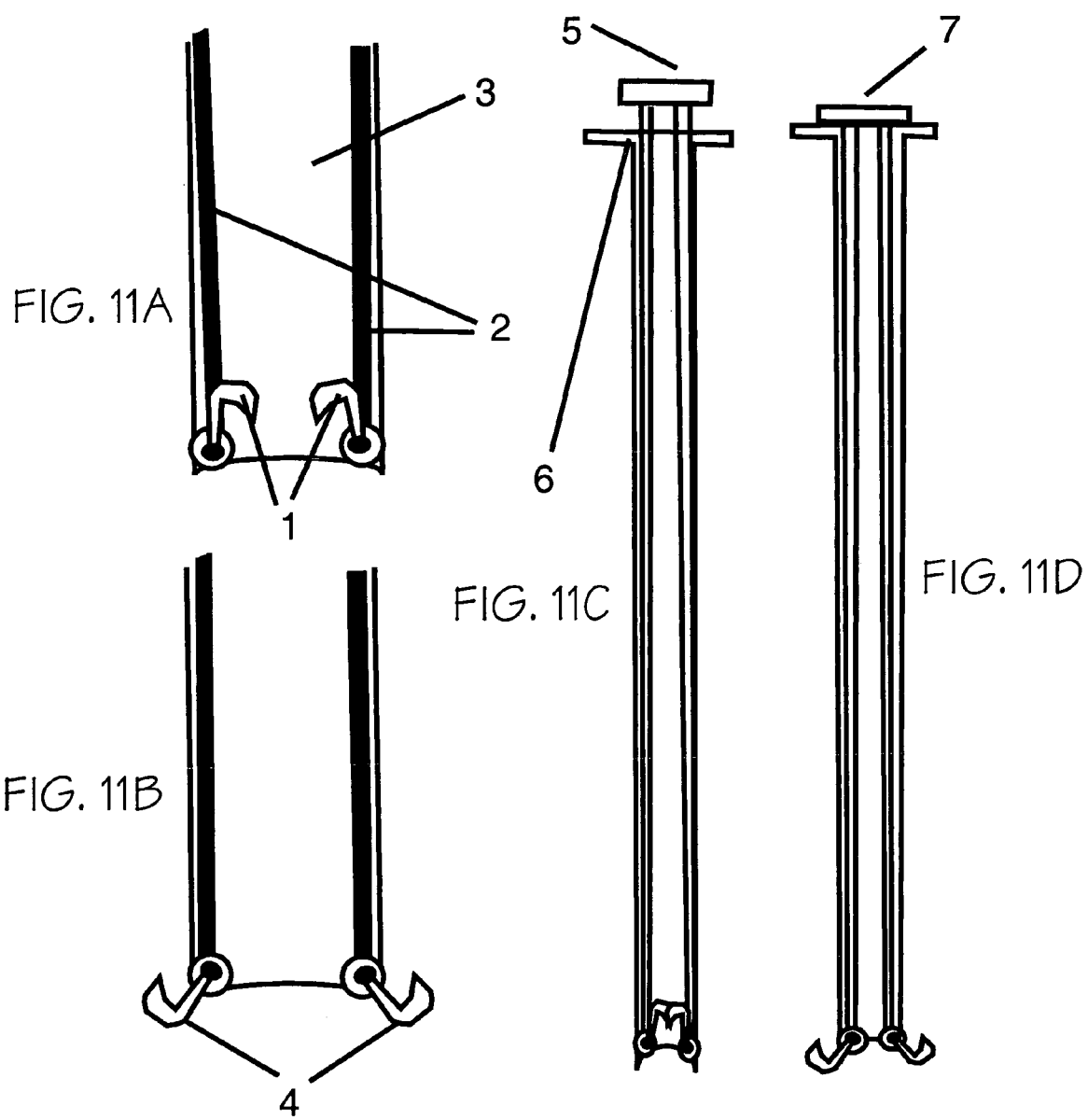

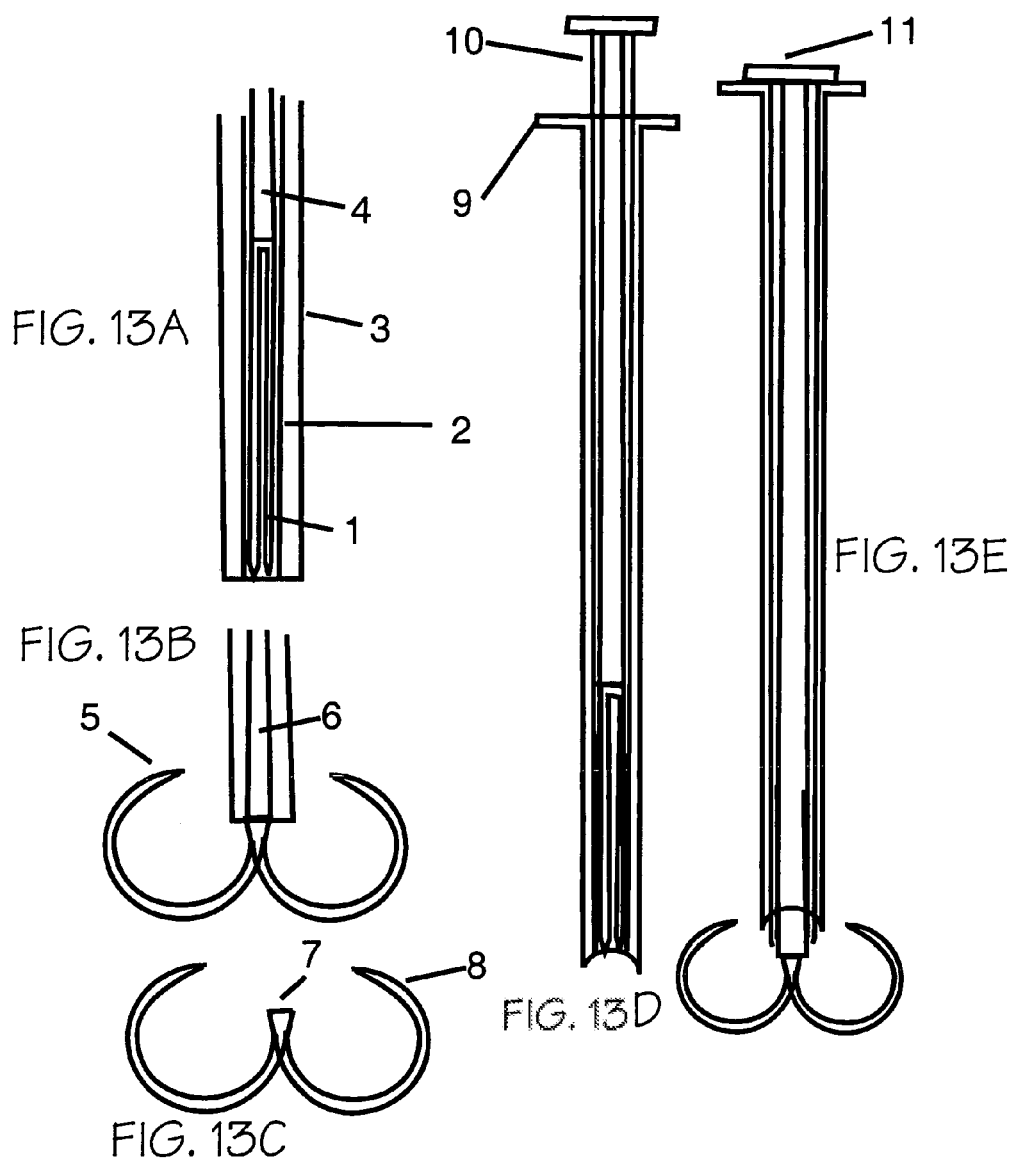

VASCULAR OPENING EDGE EVERSION METHODS AND APPARATUSES

CROSS-REFERENCE TO RELATED APPLICATIONS

This application claims priority to U.S. provisional application 60/711,279, filed Aug. 24, 2005, and to U.S. provisional application 60/726,985, filed Oct. 14, 2005, and is a continuation-in-part of U.S. utility application Ser. No. 11/316,775, filed Dec. 23, 2005 now abandoned, each of which is incorporated herein by reference.

FIELD OF THE INVENTION

The present invention relates to methods and apparatuses for closing punctures and apertures in human and animal tissue and to methods and apparatuses for inserting such an apparatus into such tissue to perform such closure functions.

BACKGROUND

During angiography and related procedures, catheters are inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, plaque removal, and infusion of a therapeutic substance. After the procedure is completed and the catheter is removed from the patient, the access hole must be closed to prevent massive hemorrhage. This is conventionally achieved by applying pressure over the blood vessel manually and then by applying a pressure bandage, compressive weight, or clamp device. With conventional methods, the rate of post-puncture hemorrhage is high, which causes considerable complications. This complication is exacerbated by the concomitant use of anticoagulant medications such as heparin or warfarin and by antiplatelet drugs, which are commonly used to treat vascular disease.

Sutures have been used to close access puncture wounds in blood vessels. U.S. 05,613,974 describes a device and method for applying sutures to a vascular puncture. US2004/0093027A1 describes barbed suture-like material that apposes the puncture site. US 2005/0121042 A1 describes a device and method for applying suture to a vascular puncture. Difficulties with these methods include the large number of steps necessary to deploy the needles, capture the suture, withdraw the suture, tie the knot, and cut the suture. In addition, the hole in the blood vessel is often widened by insertion of the instrument, and the suture remains intravascularly on the endothelial surface, and thus can be a nidus for thrombus or intravascular mural hyperplasia with later spontaneous and catastrophic closure of the vessel.

Extravascular plugs have also been proposed for closure of vascular punctures. U.S. Pat. No. 5,254,105 and U.S. Pat. No. 5,330,445 describe an extravascular plug which is slid down the external surface of the catheter or introducer and is placed into the puncture site in this manner. U.S. Pat. No. 5,643,318 relates to a similar device that has its own vessel locator device. US22022822A1 and US2004/0158287A1 describe an extravascular plug that is delivered with a specialized system. US24215232A1 describes an extravascular plug with an intravascular anchor set with a sheath with a detection port. US2005/0085855A1 describes an extravascular collagen plug, held in place with an intravascular anchor, and a device that locks over a piece of suture. U.S. Pat. No. 5,906,631 describes a plug made of hydrophilic material. U.S. Pat. No. 6,126,675 describes an intravascular anchor and a bioabsorble extravascular plug. U.S. Pat. No. 6,623,509 describes a bioabsorbable plug. U.S. Pat. No. 6,296,657 and U.S. Pat. No. 6,743,195 describe an inflatable balloon that puts pressure on the puncture site. U.S. Pat. No. 6,569,185 describes an injectable vascular plug. U.S. Pat. No. 6,663,655 describes a plug that screws in the puncture tract. US2004/0143290 A1 describes a combination of an intraluminal balloon and injectable sealant. Disadvantages to these methods are related to the high likelihood of thrombosis associated with the intravascular plug or anchor, and the presence of collagen or other bioabsorble materials which cause inflammation, activate the clotting cascade, and increase the likelihood of thrombosis, which, in an arterial system, is catastrophic.

Vascular patches have also been used for repairing blood vessels, but usually only for large areas of damage. U.S. Pat. No. 5,100,422 describes a vascular patch that is sutured to the external surface of the damaged blood vessel. U.S. Pat. No. 5,100,422 describes a vascular patch achieved by instilled adhesives and the device for doing such. These are generally impractical for catheter-based methods. U.S. Pat. No. 6,248,124 and U.S. Pat. No. 5,507,744 describe devices and methods that use electrocautery for sealing vascular punctures. This also requires a complicated device, and perforation and thrombosis are very real possibilities.

Vascular clips or staples delivered through a catheter device have also been proposed. These devices have penetrating members that bring the edges of the tissue together. U.S. Pat. No. 6,695,867 describes a clip or staple that is delivered by a specialized device. U.S. Pat. No. 6,749,622 describes a number of different clips with sharpened barbs or ends that include both intra- and extravascular portions, made of metal with memory characteristics. U.S. Pat. No. 5,861,005 describes an arterial staple that is delivered with a specialized device. U.S. Pat. No. 5,919,207 describes a stapling system based on long hooked wires that appose the surfaces, with a small staple gun to close the lesion. U.S. Pat. No. 6,022,372 describes a similar staple gun. U.S. Pat. No. 6,296,657, U.S. Pat. No. 6,663,655, and U.S. Pat. No. 6,749,621 describe a clip that is external to the vessel, but clips the two sides of the puncture together, and a device for achieving such. U.S. Pat. No. 5,782,861 and U.S. Pat. No. 5,964,782 describe clip devices composed of two or more prongs or hooks that, depending on the direction of the prongs, can clip together the puncture site from the intra- or extravascular position, through the use of a collar which forces the prongs together or other mechanisms. These clip devices are composed of thick semi-rigid material, and can be placed only with a specialized instruments, and because of the rigidity have great potential to injure or cut the blood vessel. Disadvantages of these clip devices in general include difficulty in retrieving the device if misplaced, excessive manipulation required, the thickness of the clip material which tends to cut or shear the blood vessel, the large forces that must be used to curve the staples and fix the clips, the increased possibility of tearing the blood vessel, and the general lack of control of the forces being applied to the blood vessel.

Accordingly, there is a need for methods and apparatuses that are suitable for closure of vascular punctures or other openings, and that do not suffer from the drawbacks of conventional approaches.

SUMMARY OF THE INVENTION

The present invention provides methods and apparatuses that are suitable for closure of vascular punctures or other openings, and that do not suffer from the drawbacks of conventional approaches.

An apparatus according to the present invention comprises a tool that can be inserted through a puncture wound in a blood vessel, opens within the blood vessel by the extension of multiple members, the members engage and/or penetrate the vessel wall from the intralumenal side of the blood vessel, the members bring the vessel wall into apposition by the combination of traction and the geometric shape of the members, the member can the blood vessel so that a closure device can be inserted over the apposition/eversion device, and a closure device (which could be an external suture or external clip) placed on the outside of the blood vessel where it seizes and engages the everted edges of the puncture wound as the members prevent the blood vessel wound edges from moving, and finally, removing the wound eversion device or detaching the wound eversion device leaving the closure device proximal to everted wound edges.

The present invention also comprises methods of using devices according to the present invention, and methods for bring aperture edges into apposition using devices such as those described herein.

Devices according to the present invention can utilize a contractible or expandable material, for example with memory characteristics, that allow the members of the device to open and engaed spontaneously on a puncture wound of a blood vessel. Members of such devices can have textured gripping surfaces, tissue hooks, or penetrators, to seize the vessel wall and stabilize the device. Such devices can use the spontaneous opening and closing characteristics to seize the edges of the puncture site, and close them, resulting in a complete vascular closure. Such devices can be kept in a contracted or expanded state (high energy state of a memory material) by a delivery sheath and assume its functional, closing form (low energy state of a memory material) when pushed off a delivery sheath.

BRIEF DESCRIPTION OF THE FIGURES

The invention is explained by using embodiment examples and corresponding drawings, which are incorporated into and form part of the specification.

FIGS. 1a-d are schematic illustrations of a puncture wound eversion-retraction device according to the present invention.

FIGS. 3a-d are schematic illustrations of a puncture wound eversion-retraction according to the present invention.

FIG. 10 (a,b,c,d) is a schematic illustration of an example puncture wound everter device.

FIG. 11 (a,b,c,d) is a schematic illustration of an example puncture wound everter device.

FIG. 13 (a,b,c,d,e) is a schematic illustration of an example puncture wound everter device.

DETAILED DESCRIPTION

Figure 2A:
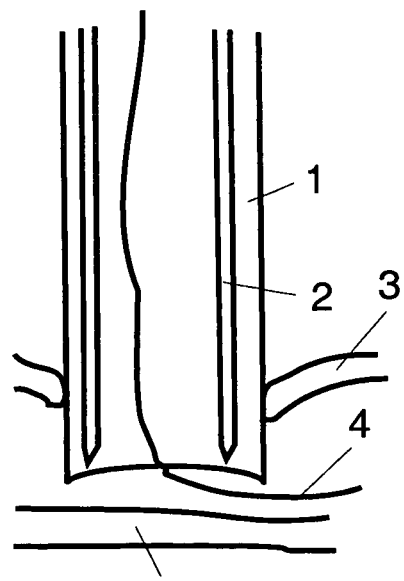
FIGS. 2a-c are schematic illustrations of a puncture wound eversion-retraction according to the present invention.

The present invention provides apparatuses and methods for closing a vascular puncture wound or any tissue aperture, for example those resulting from the insertion of a vascular catheter or surgical instrument, trauma or disease. The present invention embraces both apparatuses and methods for closing tissue openings such as vascular punctures. Devices according to the present invention can be inserted in a vascular sheath, the sheath removed or pulled back, a closure device placed over the everter device, the everted device activated by extending the graspers within the blood vessel, the graspers pulled up against and penetrate the vascular vessel wall, the wound edges everted, apposed, and brought up into the closure device, and finally the everted wound edges closed distal to the graspers by the means of an extravascular clip, extravascular suture, extravascular glue or patch, extravascular heat coagulation, or by staples or sutures that are placed through the lips of the everted wound edges. This behavior can be provided by forming at least a portion of the grasping device of a memory metal or material. The stress free state corresponds to the state at which the apparatus has closed upon the everted edges of a puncture wound of a blood vessel, and the stressed state is when the device is open and seated on the delivery sheath. Example embodiments of tissue closure apposition devices according to the present invention are shown in FIGS. 1, 2, 3, and 4. The descriptions may refer to "vessels" for convenience; the present invention is applicable to facilitate closure of various types of tissue openings.

FIG. 1(a,b,c,d) is a schematic illustration of an puncture wound everter device. FIG. 1a is a lateral view cutaway of a puncture wound everter device in the closed state (high energy state). A plurality of grasping members 101 (generally a minimum of two members, or otherwise grasping tissue at at least two locations) in the retracted state, and a sheath 102 contains grasping members. This sheath can accommodate a guidewire, or in another embodiment can be inserted through a sheath or a closure device and used like a guidewire. FIG. 1b is a lateral view of the same device in the extended or opened state (low energy state), where the grasping members 103 are extended, and curl up and engage and/or pierce the blood vessel wall. FIG. 1c is a lateral view of the everting device in the retracted state with a plunger mechanism 104 to extend the grasping members and finger flanges or rests 105 to control the device. FIG. 1d is the same device with the grasping members extended by pushing a plunger mechanism 106.

In FIG. 1 the everter device can be placed into the puncture wound by means of a guidewire that can be accommodated within the sheath 102 in which cases the everter device is placed over the guidewire and pushed through the puncture wound into the blood vessel. The closure device is then placed over the everter device and the terminal end brought up against the exterior blood vessel wall. The everter members are then extended and the device pulled up against the blood vessel wall, and the everted wound edges retracted within and held within the closure device, after which the guidewire is removed, the closure mechanism applied by the closure device causing the wound edges to be closed distally to the everting members. At this point the everter members are retracted and both the closure device and everter device removed, leaving the closure mechanism in place on the external surface of the blood vessel.

Alternatively, in FIG. 1 the everter device can be placed into the puncture wound by means of a sheath that can accommodate the everter device internally. The everter device sheath 102 is placed within the operating sheath and pushed through the existing sheath into the puncture wound and into the internal lumen of the blood vessel. The operator sheath is then removed and the closure device is then placed over the everter device with the everter device sheath being used as a guidewire. The terminal end of the closure device is brought up against the exterior blood vessel wall. The everter members of the everter device are then extended, the device pulled up against the blood vessel wall, the everter members penetrating and seizing the blood vessel wall, the everted device being partially retracted, and the everted wound edges being retracted within and held within the closure device. The closure mechanism is then applied by the closure device causing the everted wound edges to be closed distally to the everting grasping members. At this point the everter members are retracted and both the closure device and everter device removed, leaving the closure mechanism in place on the external surface of the blood vessel.

FIG. 1 presents for illustration purposes 2 active members; the device can comprise as few as two active members (or one, if it grasps the tissue at multiple locations), but can include any plurality, and as many as are practical within applicable design considerations. The tissue engagement features, shown as sharp hook-like portions of the active members in the figure, can comprise textured portions or attachments, mating portions with apposing feet, penetrating devices, hooks, teeth, or other adaptations to allow firm grip of the tissue. The members can comprise memory materials to fit within the delivery sheath, to assume a lower profile when delivered, and expanded and engage the vessel wall when extended.

Figure 2B:
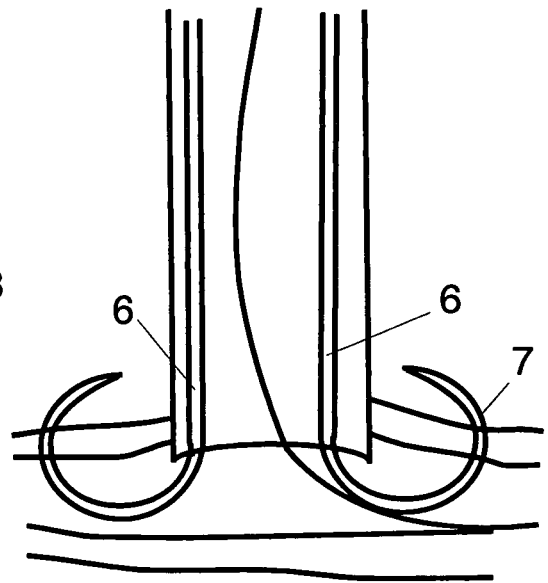
Figure 2C:
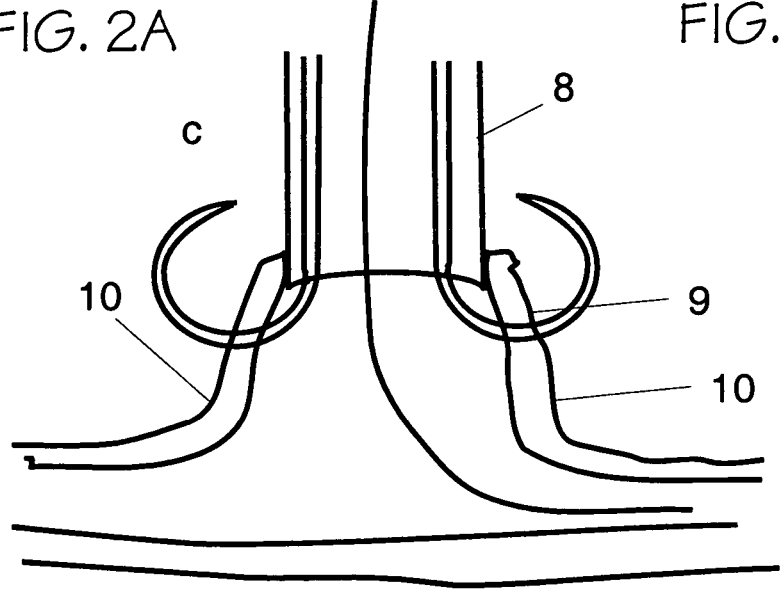
Figure 4A:
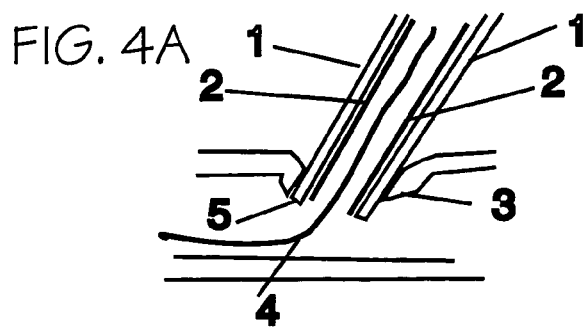
FIGS. 4a-g is are schematic illustrations of a puncture wound eversion-retraction according to the present invention.
Figure 4B:
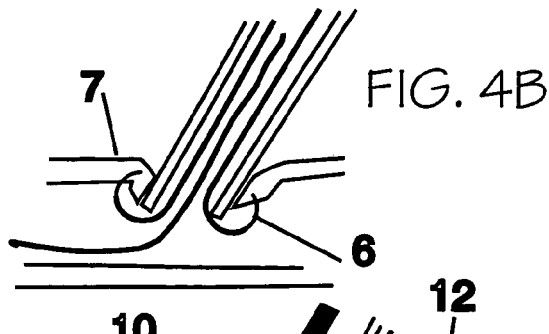
Figure 4C:
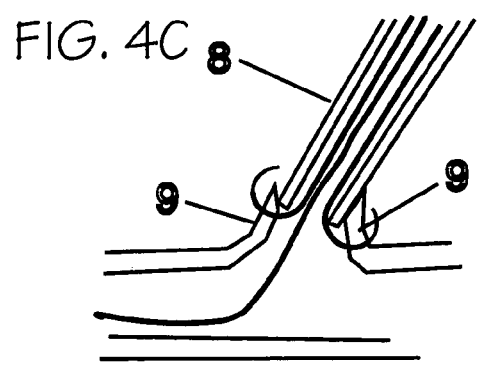
Figure 4D:
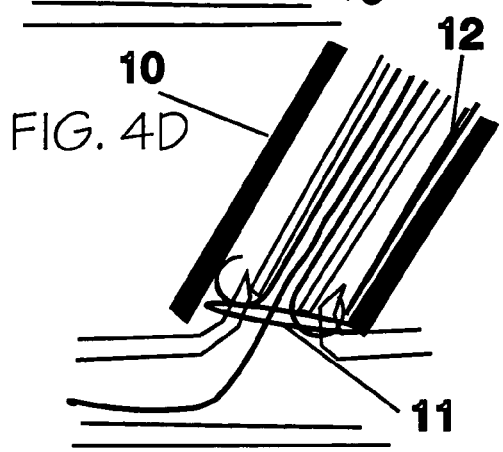
Figure 4E:
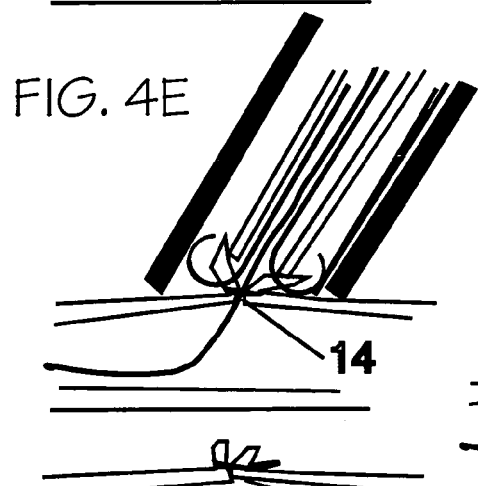
Figure 4F:
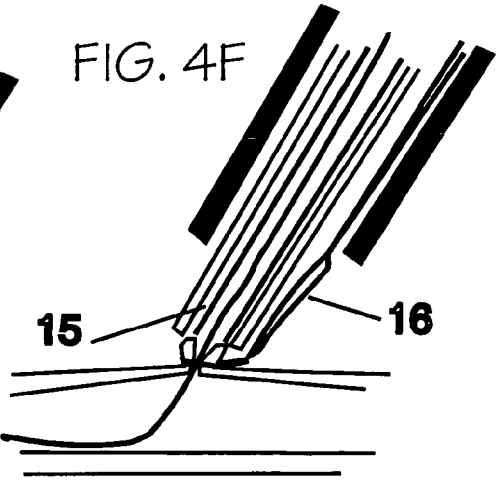
Figure 4G:

FIG. 2(a, b, c) demonstrates an example of how a puncture wound everter device according to the present invention can be used. FIG. 2a is a lateral cutaway view of the everter device after insertion into the blood vessel where FIG. 2a-1 is the everter device sheath, FIG. 2a-2 is the retracted (high energy state) grasping member, FIG. 2a-3 is the proximal vessel wall; FIG. 2a-4 is the guidewire, and FIG. 2a-5 is the distal vessel wall. FIG. 2b demonstrates the everter device with the grasping members extended where FIG. 2b-6 is the extended grasping member, and FIG. 2b-7 is the grasping member penetrating the proximal vessel wall. FIG. 2c show the everter device with traction, where FIG. 2c-8 is the everter device pulled proximately towards the operator, which enlongates, everts, apposes and hold the vessel wall FIG. 2c-9, so that a closure device can be placed on the neck of the everted wound margins FIG. 2c-10.

FIG. 3(a, b, c, d) demonstrates how an everter device according to the present invention can be used to apply an extravascular clip or stable. FIG. 3a is a lateral cutaway view, where 3a-1 is expulsion portion of the closure devices, 3a-2 is the extravascular clip or staple, and 3a-3 is the extravascular clip or staple delivery sheath. FIG. 3b is a view of the clip 3b-4 being delivered onto the neck of the everted wound edges, closing the wound 3b-5. FIG. 3c demonstrates the everter device 3c-7 with the members retracted, leaving the clip or staple closed over the guidewire 3c-8. FIG. 3d demonstrates the clip or staple left in situ, with the clip 3d-9 left in place, completely closing the puncture wound edges 3d-10.

FIG. 4(a,b,c,d,e,f,g) is a demonstration of a method to insert a closure device, in this case an extravascular suture. FIG. 4a is a lateral view where the gripper sheath 4a-1 is placed over the guidewire 4a-4, so that the distal edge of the sheath has been pushed internally relative to the proximal blood vessel war 4a-3. The gripper members 4a-2 have not been extended. In FIG. 4b the gripper tines 4b-6 are extended penetrating or gripping the proximal blood vessel wall 4b-97. In FIG. 4c traction is then placed on the gripper sheath and members 4c-8, which pull and evert the wound edges 4c-9. In FIG. 4d the suture introducer sheath 4d-10 is the placed over the gripper sheath, and the suture 4d-11 is tightened by pulling on the suture drawstring contained in 4d-12. FIG. 4e the suture is then completely closed around the guidewire 4d-14, closing the puncture. In FIG. 4f the gripper members 4f-15 are retracted within the everter gripper sheath, and the suture loop 4f-16 is cut. In FIG. 4g, if there is no bleeding, the guidewire is removed leaving 4g-17 an external suture closure of the blood vessel puncture wound.

Figure 5A:
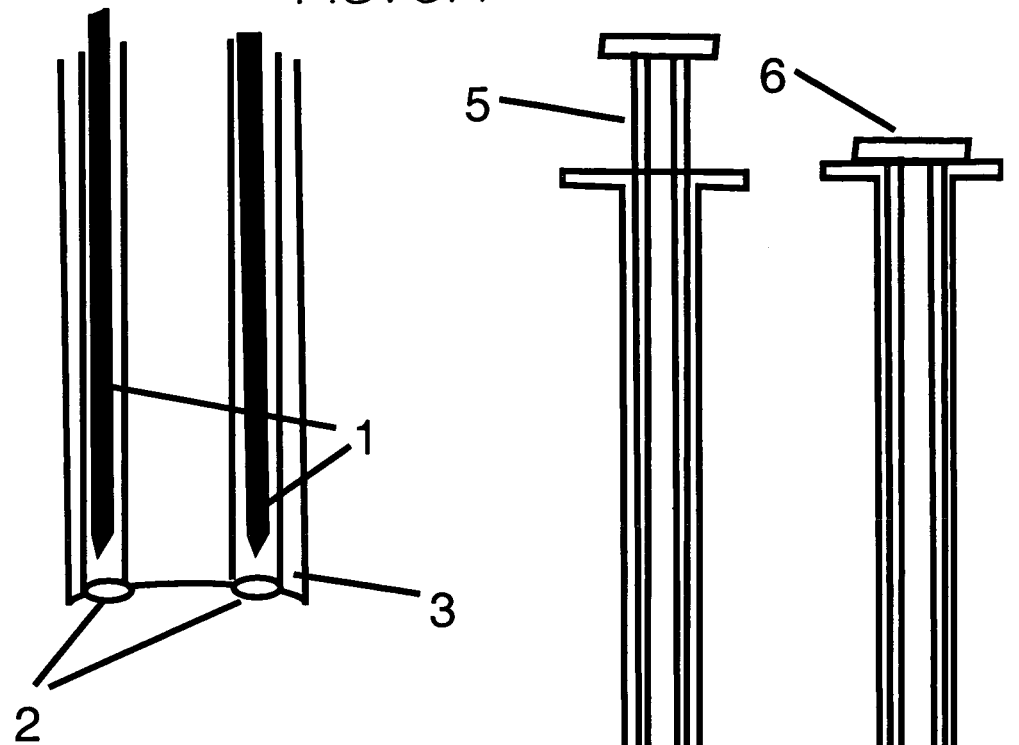
FIG. 5 (a,b) is a schematic illustration of a puncture wound eversion-retraction according to the present invention.
Figure 5B:
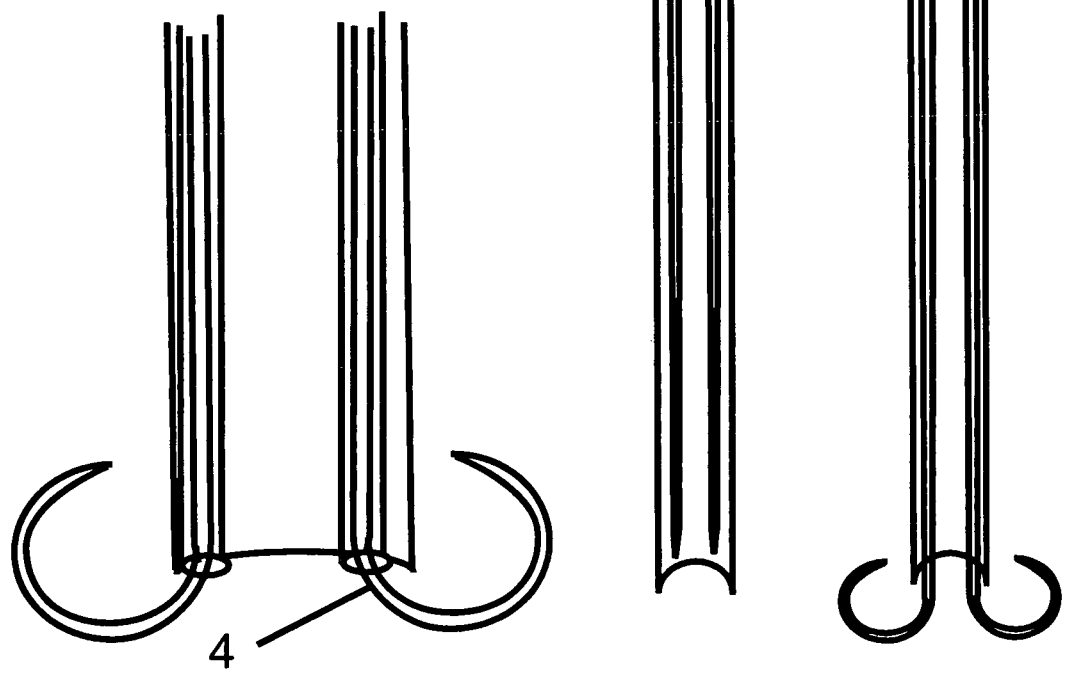

FIG. 5(a,b) is another schematic illustration of a puncture wound everter device, similar to that of FIG. 1. FIG. 5a is a lateral view cutawary of a puncture wound everter device in the closed state (high energy state). FIG. 5a-1 are the plurality of grasping members (comprising a minimum of two members) in the retracted state; these are constrained within internal lumen FIG. 5a-2, which are held within the everter device sheath. FIG. 5a-3 is the sheath that contains grasping members. This sheath can accommodate a guidewire, or in another embodiment can be inserted through a sheath or a closure device and used like a guidewire. FIG. 5b is a lateral view of the same device in the extended or opened state (low energy state), where the grasping members 5b-4 are extended, and curl up and engage and/or pierce the blood vessel wall. This device would otherwise be inserted, operated, and used identically to the embodiment in FIG. 1. FIG. 5 presents for illustration purposes two active members; the device can comprise as few as two active members, but can include any plurality, and as many as are practical within applicable design considerations. The tissue engagement features, shown as sharp hook-like portions of the active members in the figure, can comprise textured portions or attachments, mating portions with apposing feet, penetrating devices, hooks, teeth, or other adaptations to allow firm grip of the tissue. The members can comprise memory materials to fit within the delivery sheath, to assume a lower profile when delivered, and expanded and engage the vessel wall when extended.

Figure 6A:
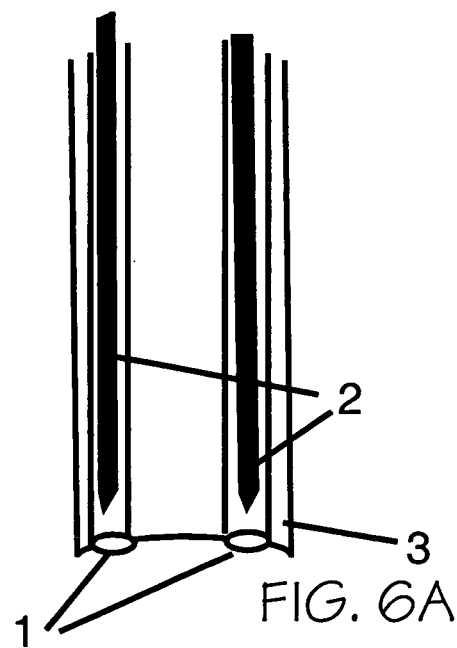
FIG. 6 (a,b) is a schematic illustration of a puncture wound eversion-retraction according to the present invention.
Figure 6B:
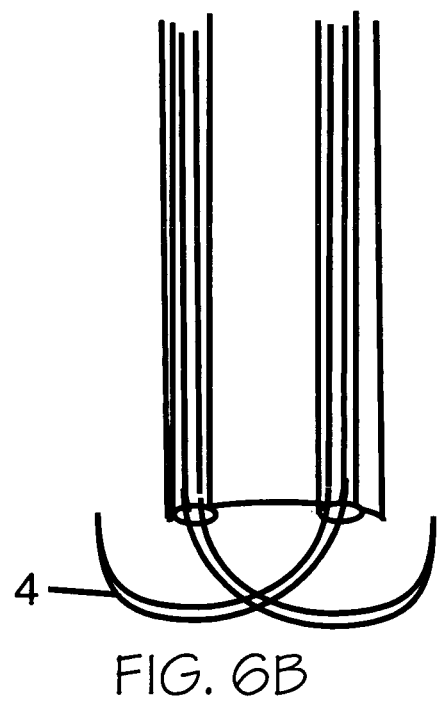

FIG. 6(a,b) is another schematic illustration of a puncture wound everter device, similar to that of FIG. 1. FIG. 6a is a lateral view cutaway of a puncture wound everter device in the closed state (high energy state). FIG. 6a-1 are the plurality of grasping members (comprising a minimum of two members) in the retracted state; these are constrained within internal lumen FIG. 6a-2 (or not), which are held within the everter device sheath FIG. 6a-3 is the sheath that contains grasping members. In this case the members are extended in a crosswise function across the sheath, the purpose being that the wound edges are more efficiently and mechanically brought into apposition by the method of retraction. The sheath can accommodate a guidewire, or in another embodiment can be inserted through a sheath or a closure device and used like a guidewire. FIG. 6b is a lateral view of the same device in the extended or opened state (low energy state), where the grasping members 6b-4 are extended, and curl up and engage and/or pierce the blood vessel wall. This device would otherwise be inserted, operated, and used identically to the embodiment in FIG. 1. FIG. 6 presents for illustration purposes two active members; the device can comprise as few as two active members, but can include any plurality, and as many as are practical within applicable design considerations. The tissue engagement features, shown as sharp hook-like portions of the active members in the figure, can comprise textured portions or attachments, mating portions with apposing feet, penetrating devices, hooks, teeth, or other adaptations to allow firm grip of the tissue. The members can comprise memory materials to fit within the delivery sheath, to assume a lower profile when delivered, and expanded and engage the vessel wall when extended.

Figure 7A:
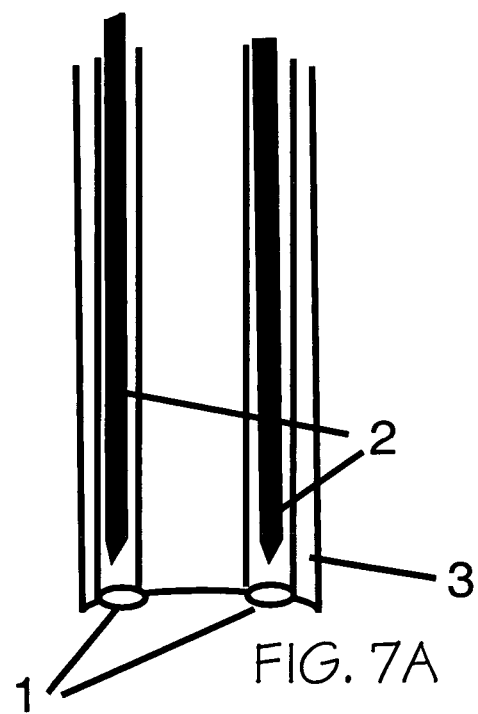
FIG. 7 (a,b) is a schematic illustration of eversion and retraction of the edges of a tissue opening using a device according to the present invention.
Figure 7B:
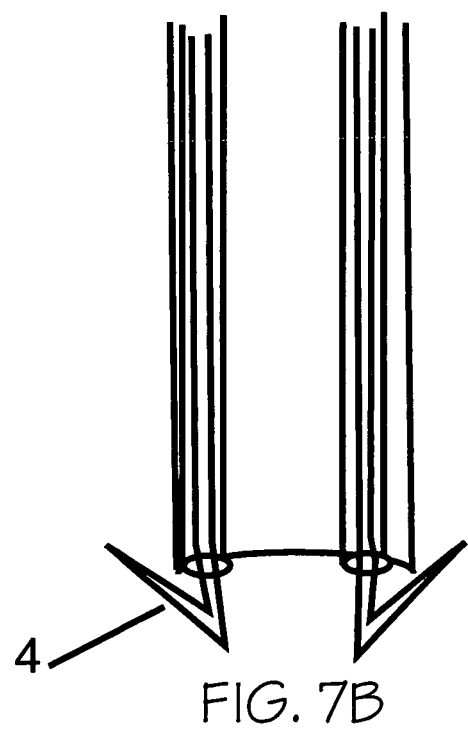
Figure 8A:
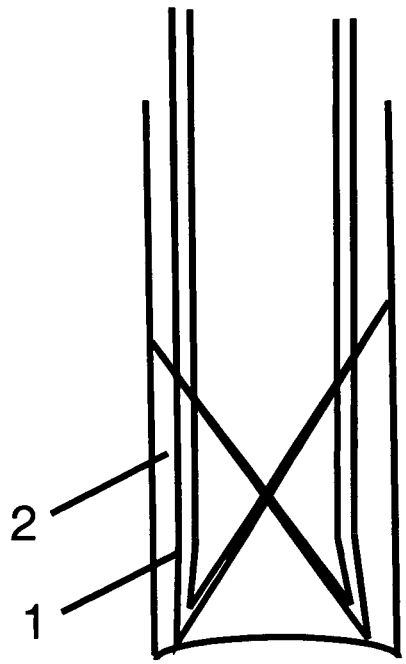
FIG. 8 (a,b,c,d) is a schematic illustration of steps in a method of closing a tissue opening according to the present invention.
Figure 8C:
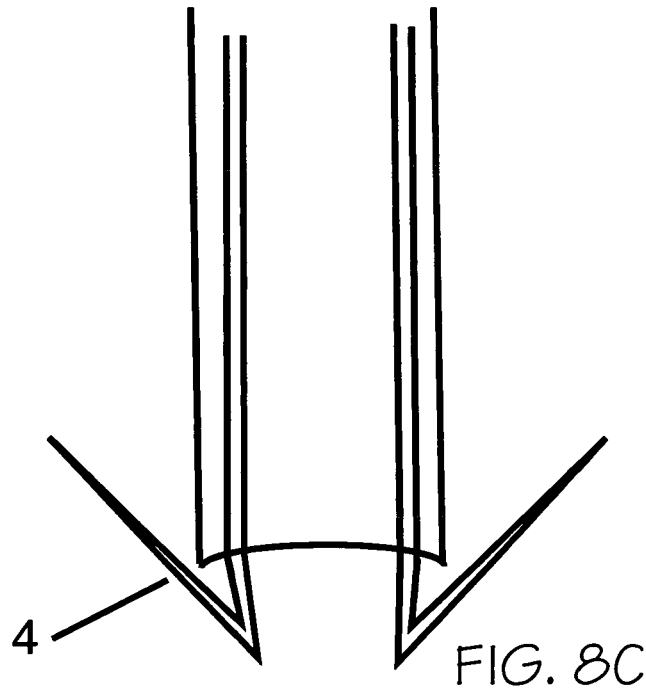
Figure 8D:
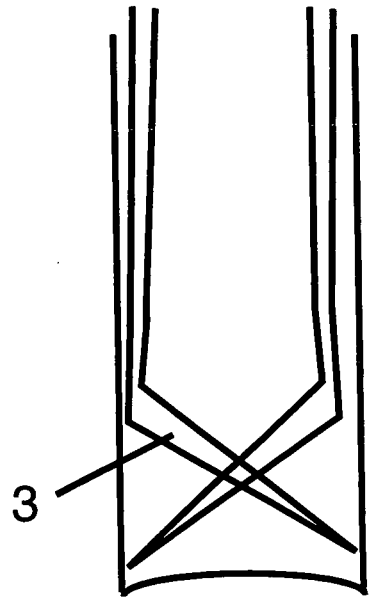
Figure 8D:
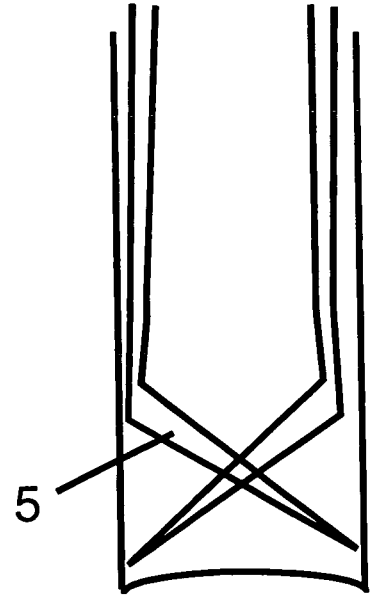

FIG. 7(a,b) is another schematic illustration of an puncture wound everter device, similar to that of FIG. 1. FIG. 7a is a lateral view cutaway of a puncture wound everter device in the closed state (high energy state). FIG. 7a-1 are the plurality of grasping members (comprising a minimum of two members) in the retracted state; these are constrained within internal lumen FIG. 7a-2 (or not), which are held within the everter device sheath FIG. 7a-3 is the sheath that contains grasping members. In this case the members are comprised at a sharp geometric angle. The sheath can accommodate a guidewire, or in another embodiment can be inserted through a sheath or a closure device and used like a guidewire. FIG. 7b is a lateral view of the same device in the extended or opened state (low energy state), where the grasping members 7b-4 are extended, and curl up and engage and/or pierce the blood vessel wall. This device would otherwise be inserted, operated, and used identically to the embodiment in FIG. 1. FIG. 7 presents for illustration purposes two active members; the device can comprise as few as two active members, but can include any plurality, and as many as are practical within applicable design considerations. The tissue engagement features, shown as sharp hook-like portions of the active members in the figure, can comprise textured portions or attachments, mating portions with apposing feet, penetrating devices, hooks, teeth, or other adaptations to allow firm grip of the tissue. The members can comprise memory materials to fit within the delivery sheath, to assume a lower profile when delivered, and expanded and engage the vessel wall when extended.

FIG. 8(a,b,c,d) is a schematic illustration of an puncture wound everter device. FIG. 8a is a lateral view cutaway of a puncture wound everter device in the closed state (high energy state). FIG. 8a-1 are the plurality of grasping members (comprising a minimum of two members) in the retracted state; in this case, the members are flexed back within the sheath; and FIG. 8a-2 is the sheath that contains grasping members. This sheath can accommodate a guidewire, or in another embodiment can be inserted through a sheath or a closure device and used like a guidewire. FIG. 8b is a lateral view of the same device in the retracted or closed states state (low energy state), where the grasping members 8b-3 flexed forward. FIG. 8c is a lateral view of the same device in the extended or opened state (low energy state), where the grasping members 8b-4 are extended, and flex up and engage and/or pierce the blood vessel wall which represents the extended form of the devices shown in FIG. 8a and FIG. 8b. FIG. 8d is a lateral view of the same device in the retracted or closed state (high energy state), where the grasping members 8d-5 are retracted, and flexed down which represents the retracted form of the devices shown in FIG. 8a and FIG. 8b.

Figure 9A:
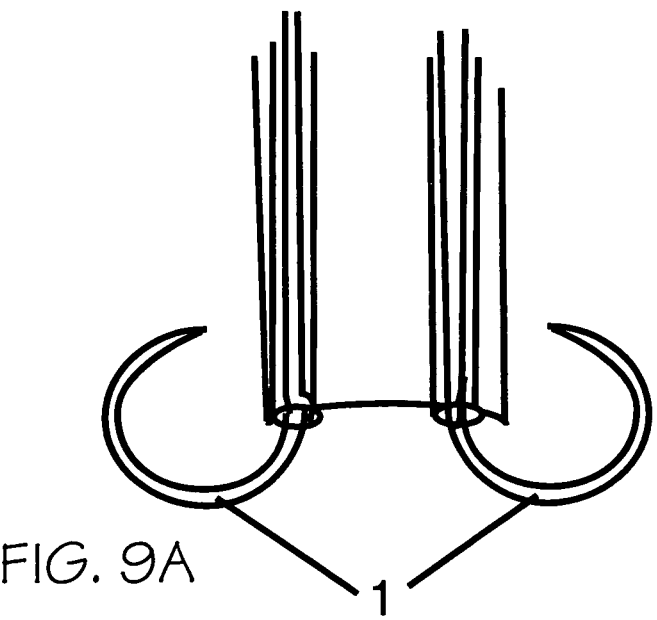
FIG. 9 (a,b) is a schematic illustration of steps in a method of closing a tissue opening according to the present invention.
Figure 9B:
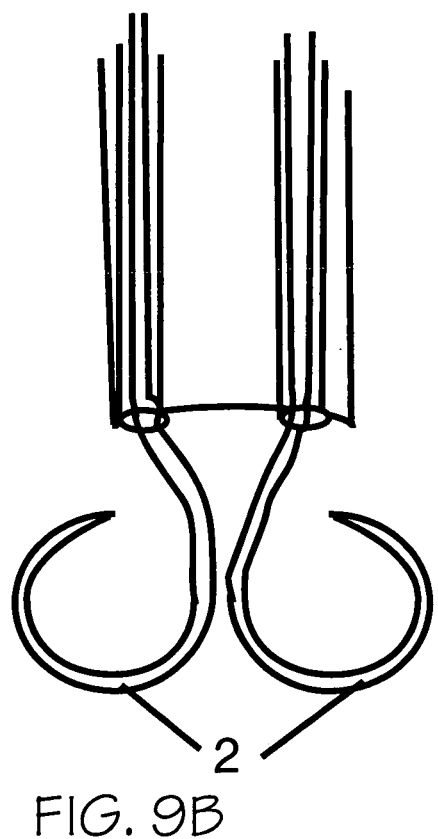
Figure 12A:
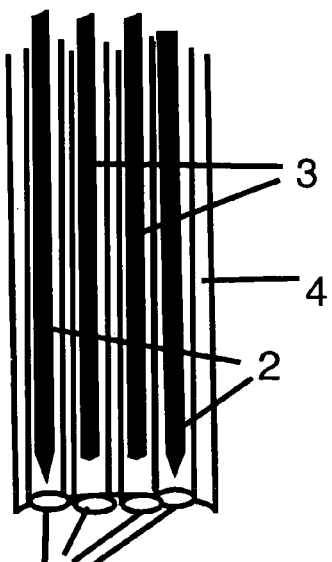
FIG. 12 (a,b,c,d) is a schematic illustration of an example puncture wound everter device.
Figure 12B:
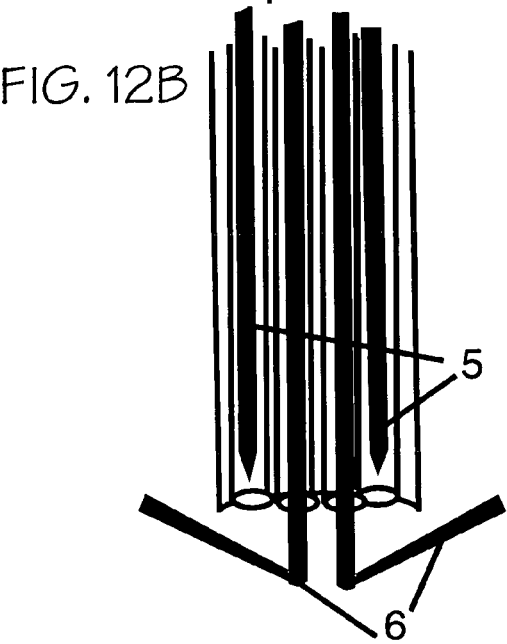
Figure 12C:
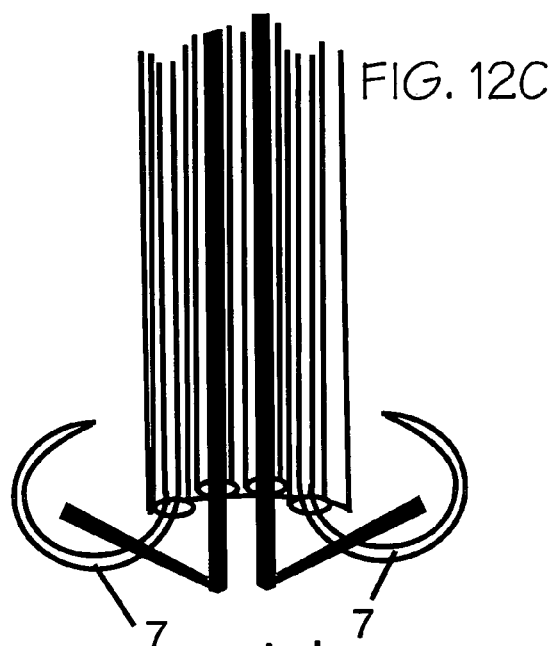
Figure 12D:
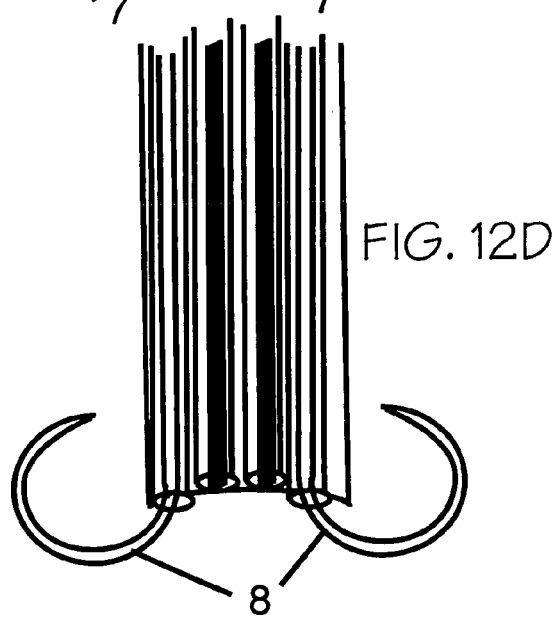
Figure 14A:
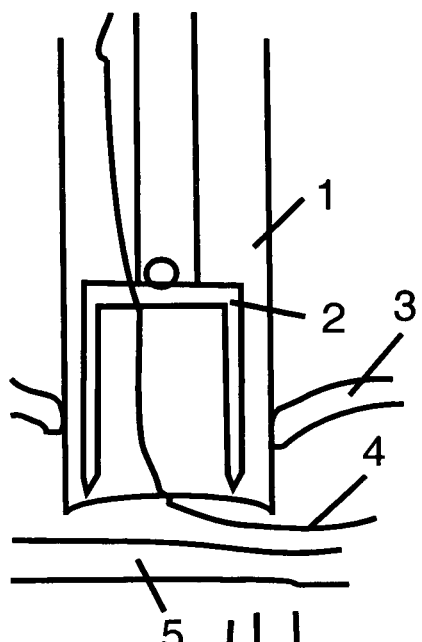
FIG. 14 (a,b,c,d) is a view of another example embodiment of a gripper device with a residing memory gripper being used.
Figure 14B:
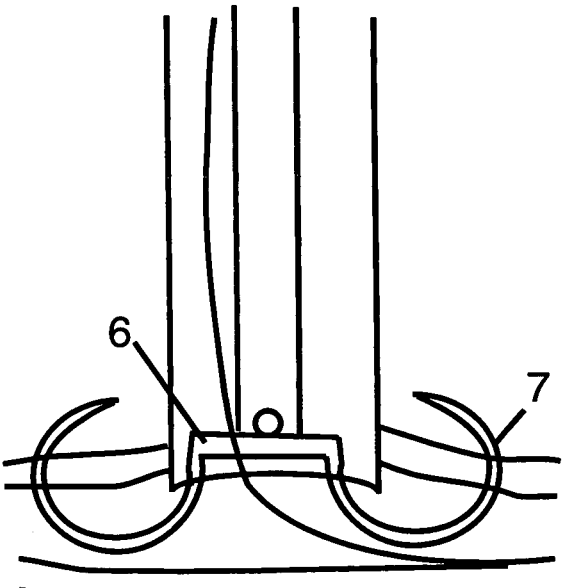
Figure 14C:
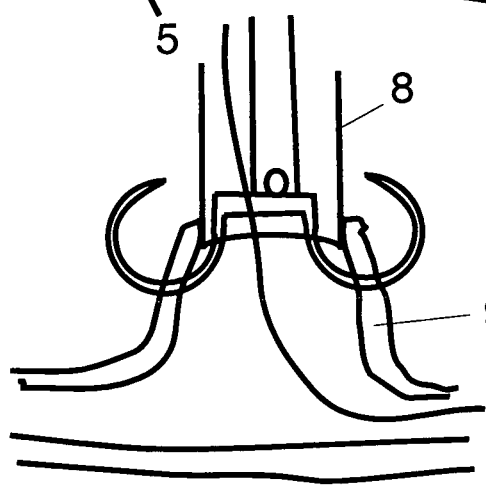
Figure 14D:
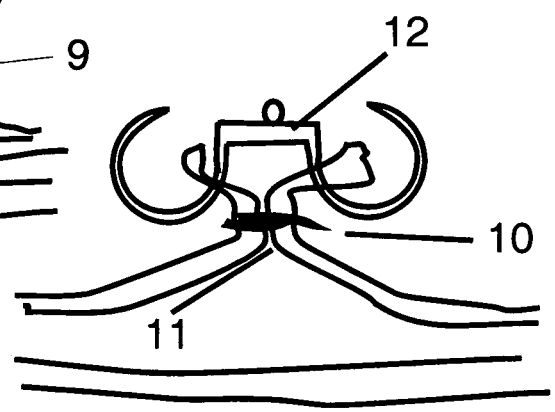

FIG. 9(a,b) is another schematic illustration of an puncture wound everter device, similar to that of FIG. 1. FIG. 9a is a lateral view cutaway of a puncture wound everter device in the partially opened state (half-way to low energy state). FIG. 9a-1 are the plurality of grasping members (comprising a minimum of two members) in the partially extended state. FIG. 9b is a lateral view of the same device in the fully extended or opened state (low energy state), where the grasping members 9b-2 are extended, and curl towards each other after then have engaged and/or pierced the blood vessel wall. In this case the members when fully extended move towards the midline of the sheath, the purpose being that the wound edges are more efficiently and mechanically brought into apposition during extension and retraction. This device would otherwise be inserted, operated, and used identically to the embodiments in the prior examples. FIG. 9 presents for illustration purposes two active members; the device can comprise as few as two active members, but can include any plurality, and as many as are practical within applicable design considerations. The tissue engagement features, shown as sharp hook-like portions of the active members in the figure, can comprise textured portions or attachments, mating portions with apposing feet, penetrating devices, hooks, teeth, or other adaptations to allow firm grip of the tissue. The members can comprise memory materials to fit within the delivery sheath, to assume a lower profile when delivered, and expanded and engage the vessel wall when extended.

FIG. 10(a,b,c,d) is a schematic illustration of an example puncture wound everter device. FIG. 10a is a lateral view cutaway of a puncture wound everter device in the closed state (high energy state). FIG. 10a-1 are the plurality of grasping members (comprising a minimum of two members) in the retracted state; in this case, the members are closed within an internal lumen 10a-2 and/or with the sheath 10a-3. The grasping members are attached to a solid member 6a-4 which can be a solid or hollow columnar device with an internal lumen for a guidewire, or can be a wire in itself. This sheath can accommodate a guidewire, or in another embodiment can be inserted through a sheath or a closure device and used like a guidewire. FIG. 10b is a lateral view of the same device in the extended or open state (low energy state), where the grasping members 6b-5 are extended into their grasping or extended position. FIG. 10c is a lateral view of the everting device in the retracted state with a plunger mechanism FIG. 10c-6 to extend the grasping members and finger flanges or rests FIG. 10c-7 to control the device. FIG. 10d is the same device with the grasping members extended by pushing the plunger mechanism FIG. 10d-7.

FIG. 11(a,b,c,d) is a schematic illustration of an example puncture wound everter device. FIG. 11a is a lateral view cutaway of a puncture wound everter device in the closed state (high energy state). FIG. 11a-1 are a plurality of grasping members (comprising a minimum of two members) in the retracted state; in this case, the members can rotate from internally to externally upon each upon an axis moved by a mechanical mechanism 11a-2 (which could be a flywheel mechanism or gear and groove axel mechanism) all which are closed within an internal lumen 11a-3 and/or with the sheath 11a-3. FIG. 11b is a lateral view of the same device in the extended or open state, where the grasping members 11b-4 are extended into their grasping or extended position. FIG. 11c is a lateral view of the everting device in the retracted state with a plunger mechanism FIG. 11c-5 to extend the grasping members, and finger flanges or rests FIG. 11c-6 to control the device. FIG. 11d is the same device with the grasping members extended by pushing the plunger mechanism FIG. 11d-6.

FIG. 12(a,b,c,d) is a schematic illustration of an example puncture wound everter device. FIG. 12a is a lateral view cutaway of a puncture wound everter device in the closed state (high energy state) that is placed through a puncture wound within the blood vessel. FIG. 12a-1 are internal lumina for the plurality of grasping members 12a-2 (comprising a minimum of two members) in the retracted state; at least two parallel locator members are also present 12a-3 in their lumina within the everter device sheath 12a-4. FIG. 12b demonstrates that the grasping members 12b-5 have not been extended, while the locator members 12b-6 have been extended. As can be seen, these do not have penetrating surfaces. The locator members are pulled up against the internal edges of the puncture wound, locating the wound margins. In FIG. 12c, once the wound margins have been located the grasping members are extended 12c-7, and these penetrate and grasp the proximal vessel wall. In FIG. 12d once the vessel is grasped by the grasping members 12d-8, the locator members are re-retracted, and the device is then used identically to the other examples.

FIG. 13(a,b,c,d,e) is a schematic illustration of an example puncture wound everter device. FIG. 13a is a lateral view cutaway of a puncture wound everter device in the closed state (high energy state) that is placed through a puncture wound within a blood vessel. FIG. 13a-1 shows the plurality of grasping members (comprising a minimum of two members) in the retracted state within an internal lumen 13a-2 within the everter device sheath 13a-3. The grasping members 13a-1 are attached to an internal columnar structure 13a-4. FIG. 13b illustrates the grasping members 13b-5 extended, by action of the internal columnar structure 13a-6 being extended. FIG. 13c illsutrates the grasping members 13c-8 detached from the columnar structure at the mating area 13c-7 and expelled independently. FIG. 13d is a lateral view of the everting device in the retracted state with a plunger mechanism 13d-10 to extend the grasping members and finger flanges or rests FIG. 13d-9 to control the device. FIG. 13d is the same device with the grasping members extended by pushing the plunger mechanism 13d-11.

FIG. 14(a, b, c, d) is a view of another example embodiment of a gripper device with a residing memory gripper being used. In FIG. 14a the gripper device sheath 14a-1 with the residing gripper 14a-2 with columnar connecter is introduced into the blood vessel 14a-3 over the guidewire 14a-4. In FIG. 14b after introduction, the gripper 14b-6 is expelled from the sheath, and the gripping members then penetrate and grip 14b-7 the proximal tissue surrounding the puncture wound. In FIG. 14c traction (pulling) is placed on the 14c-8 gripper sheath and gripper members on the columnar base, everting the wound edges 14c-9. In FIG. 14d a closure device 14d-10 is placed over the gripper device and closed on the neck of the everted wound edges, closing the wound edges 14d-11. The gripping device 14d-12 is detached from the columnar holder and is held in place and prevented from migrating internally by the closure device 14d-10 and the closure device is prevented from migrating externally by the gripping device 14-d12. Thus, this is a combination of a clip and a suture.

Any part of an apparatus according to the present invention can be made from any of a number of suitable materials, or combinations thereof. In some applications, it can be desirable for members to be of radioopaque materials or be coated to be made radioopaque. Members can be made from bioabsorbable polymers or compounds, non-absorbable alloys and compounds including stainless steel, MP35, Nitinol, Nickel-Titanium alloy, Kevlar, nylon polyester acrylic, gold, platinum, tantalum, niobium, molybdenum, rhodium, palladium silver, hafnium, tungsten, iridium. Materials with memory can be useful, where the memory property can provide force for activation of the active members from the open to the closed state. Members can be made in the form of wires, fibers, filaments, small beams, and other extruded, woven, or formed shapes. Examples of suitable materials include piano wire, super elastic memory wire, chromium allows, alloys of titanium and nickel, and other elastic memory materials. A suitable fabric or coating can be made from a number of suitable materials; in some applications it can be desirable to use flexible polymeric materials with elastomeric properties including polyurethane, polyethylene, polyestenurethane, polyimide, olyethreimide, polycarbonate, polysiloxane, polyvinyls, hydroxyethylmethacrylate, related polymers, copolymers of these or other polymers, or drug-embedded or drug-eluting polymers to prevent coagulation or intimal hyperplasia (such as Taxol), which can be made radioopaque by markers to addition of appropriate radiopaque materials.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A tissue eversion device, comprising:
a) a delivery sheath having a distal end;
b) a tissue engaging element extending from a proximal end to the distal end of the delivery sheath, the tissue engaging element having a plurality of elongated members extending distally from the proximal end of the delivery sheath each having a tissue penetrating feature, the tissue engaging element has a first configuration wherein it is contained within the delivery sheath and a second configuration wherein each of the tissue penetrating feature extends distally beyond the distal end of an outer surface of the delivery sheath, wherein in the second configuration an intermediate portion of each elongate member extends distally from the distal end of the delivery sheath towards a longitudinal midline of the delivery sheath with an end portion of the intermediate portion being closer to the longitudinal midline than an end portion of the elongate member adjacent the distal end of the delivery sheath, and a curved end portion, extending from the end portion of the intermediate portion of each elongate member, is curled outwardly from the intermediate portion and then towards the longitudinal midline of the delivery sheath to terminate at a location spaced apart from the intermediate portion and form an open curved portion.

2. A tissue eversion device as in claim 1, wherein each elongated member has an end adapted to engage tissue, wherein the elongated members reside within the delivery sheath substantially parallel to an axis of the delivery sheath when in the first configuration, and wherein the elongated members curve away from the axis when in the second configuration.

3. A tissue eversion device as in claim 2, wherein the elongated members have sharpened ends.

4. A tissue eversion device as in claim 1, wherein the tissue engaging element comprises metal.

5. A tissue eversion device as in claim 1, wherein the tissue engaging element comprises bioabsorbable polymer, bioabsorbable compound, non-absorbable alloy, non-absorbable compound, stainless steel, MP35, Nitinol, Nickel-Titanium ally, Kevlar, nylon polyester acrylic, gold, platinum, tantalum, niobium, molybdenum, rhodium, palladium silver, hafnium, tungsten, iridium, artificial muscle, shape memory alloy, or a combination thereof.

6. A tissue eversion device as in claim 1, wherein the tissue engaging element comprises a fixture adapted to attach to a retracting element.

7. A tissue eversion device as in claim 1, wherein the tissue engaging element is moveable relative to the delivery sheath along an axis of the delivery sheath, and wherein motion of the tissue engaging element along the axis past the end of the delivery sheath allows the tissue engaging element to attain the second configuration, and wherein motion of the tissue engaging element into the end of the delivery sheath causes the tissue engaging element to attain the first configuration.

8. A tissue eversion device as in claim 1, wherein the elongated members flex or curl outwards relative to the delivery sheath to attain the second configuration.

9. A tissue eversion device as in claim 1, wherein the tissue engaging element can be actuated to attain the second configuration by action of a plunger and flanges mounted with the device.

10. A tissue eversion device as in claim 1, wherein the elongated members are movably mounted within individual lumens within the delivery sheath.

11. A tissue eversion device, comprising:
a) a delivery sheath having a distal end;
b) a plurality of elongated members extending distally from a proximal end of the delivery sheath to the distal end and each having a tissue penetrating feature, each elongated member of the plurality of elongated members has a first configuration wherein it is contained within the delivery sheath and a second configuration where the elongated member extends distally beyond the distal end of the outer surface of the delivery sheath, wherein in the second configuration an intermediate portion of each elongate member extends distally from the distal end of the delivery sheath towards a longitudinal midline of the delivery sheath with an end portion of the intermediate portion being closer to the longitudinal midline than an end portion of the elongate member adjacent the distal end of the delivery sheath, and a curved end portion of the intermediate portion of each elongate member is curled outwardly from and then towards the longitudinal midline of the delivery sheath to terminate at a location spaced apart from the intermediate portion and form an open curved portion, the intermediate portion being proximal to the curved end portion curling outwardly from the longitudinal midline of the delivery sheath.

12. A tissue eversion device as in claim 11, wherein the tissue penetrating feature is a sharp hook-like portion, a textured portion, hooks, or teeth.

13. A tissue eversion device as in claim 12, wherein the elongated members reside within the delivery sheath substantially parallel to an axis of the delivery sheath when in the first configuration and wherein the elongated members curve away from the axis when in the second configuration.

14. A tissue eversion device as in claim 11, wherein the elongated members comprise metal.

15. A tissue eversion device as in claim 11, wherein the elongated members comprise bioabsorbable polymer, bioabsorbable compound, non-absorbable alloy, non-absorbable compound, stainless steel, MP35, Nitinol, Nickel-Titanium ally, Kevlar, nylon polyester acrylic, gold, platinum, tantalum, niobium, molybdenum, rhodium, palladium silver, hafnium, tungsten, iridium, artificial muscle, shape memory alloy, or a combination thereof.

16. A tissue eversion device as in claim 11, wherein the elongated members are moveable relative to the delivery sheath along an axis of the delivery sheath, and wherein motion of the elongated members along the axis past the end of the delivery sheath allows the elongated members to attain the second configuration, and wherein motion of the elongated members into the end of the delivery sheath causes the elongated members to attain the first configuration.

17. A tissue eversion device as in claim 11, wherein the first configuration is a high energy retracted state and the second configuration is a low energy extended state.

18. A tissue eversion device as in claim 11, comprising two lumens disposed within the delivery sheath, each lumen configured to receive one of the plurality of elongated members.

19. A tissue eversion device as in claim 11, wherein the plurality of elongated members can be actuated to attain the second configuration by action of a plunger and flanges mounted with the device.

* * * * *